United States Patent
Lee

(10) Patent No.: US 10,555,794 B2
(45) Date of Patent: Feb. 11, 2020

(54) DEVICES FOR CONDUCTING SUBPERIOSTEAL MINIMALLY INVASIVE AESTHETIC JAW BONE GRAFTING AUGMENTATION AND THEIR USE

(71) Applicant: Ernesto A. Lee, Bryn Mawr, PA (US)

(72) Inventor: Ernesto A. Lee, Bryn Mawr, PA (US)

(*) Notice: Subject to any disclaimer, the term of this patent is extended or adjusted under 35 U.S.C. 154(b) by 191 days.

(21) Appl. No.: 15/493,961

(22) Filed: Apr. 21, 2017

(65) Prior Publication Data

US 2017/0296308 A1    Oct. 19, 2017

Related U.S. Application Data

(63) Continuation of application No. PCT/US2017/025478, filed on Mar. 31, 2017.
(Continued)

(51) Int. Cl.
*A61C 8/02* (2006.01)
*A61C 8/00* (2006.01)
(Continued)

(52) U.S. Cl.
CPC ........ *A61C 8/0006* (2013.01); *A61B 17/1673* (2013.01); *A61C 8/0089* (2013.01);
(Continued)

(58) Field of Classification Search
CPC ................. A61C 8/0006; A61B 17/1673
See application file for complete search history.

(56) References Cited

U.S. PATENT DOCUMENTS 1,608,275 A    2/1922  Grier et al.

1,875,680 A  *  9/1932  Van Horn .......... A61C 13/0028
30/314
(Continued)

FOREIGN PATENT DOCUMENTS

WO    WO 2014033898 A1    3/2014
WO    WO2014033898 A1    3/2014
(Continued)

OTHER PUBLICATIONS

Michael S. Block, DMD et al.; Horizontal Ridge Augmentation Using Human Mineralized Particulate Bone: Preliminary Results; American Association of Oral Maxillofacial Surgeons, 2004; J Oral Maxillofac Surg 62:67-72, 2004, Suppl 2.
(Continued)

*Primary Examiner* — Andrew Yang
(74) *Attorney, Agent, or Firm* — Bonini IP Law, LLC; Frank J. Bonini, Jr.

(57) ABSTRACT

Devices for carrying out subperiosteal minimally invasive jaw bone augmentation and reconstruction procedures, to develop a passageway and surgical site in a concealed area of patient tissue, where the surgical site is not exposed. The devices have shanks with specially configured tips to facilitate maneuvering the device through mammalian tissue to develop a tunnel in the tissue and a remote surgical site within the tissue. The device tips have one or more peripheral cutting surfaces that direct the positioning of the tunnel formation when the instrument handle is manipulated, e.g., by rotation, angular, forward or rearward motion. Embodiments of the devices are configured with tips that have a wide spread for cutting and elevating tissue, and with tips that may be maneuvered to condense bone graft material being implanted at a surgical site concealed within the tissue.

31 Claims, 16 Drawing Sheets

Related U.S. Application Data

(60) Provisional application No. 62/316,140, filed on Mar. 31, 2016.

(51) Int. Cl.
*A61F 2/00* (2006.01)
*A61B 17/16* (2006.01)
*A61F 2/28* (2006.01)
*A61B 90/00* (2016.01)
*A61B 17/58* (2006.01)

(52) U.S. Cl.
CPC .......... *A61F 2/0059* (2013.01); *A61F 2/2803* (2013.01); *A61B 17/58* (2013.01); *A61B 2090/062* (2016.02); *A61F 2002/2835* (2013.01); *A61F 2002/2889* (2013.01)

(56) References Cited

U.S. PATENT DOCUMENTS

| | | |
|---|---|---|
| 4,315,745 A | 2/1982 | Murata |
| 4,340,060 A | 7/1982 | Berke et al. |
| 4,820,306 A | 4/1989 | Gorman et al. |
| 5,085,638 A | 2/1992 | Farbstein et al. |
| 5,295,827 A | 3/1994 | Fundingsland et al. |
| 5,372,503 A | 12/1994 | Elia |
| 5,695,338 A | 12/1997 | Robert |
| 6,086,592 A | 7/2000 | Rosenberg et al. |
| 6,102,932 A | 8/2000 | Kurz |
| 6,273,720 B1 | 8/2001 | Spalten |
| 6,309,219 B1 | 10/2001 | Robert |
| 6,554,803 B1 | 4/2003 | Ashman |
| 6,575,749 B1 | 6/2003 | Greenwald |
| 6,926,699 B2 | 8/2005 | Stone |
| 6,994,548 B2 | 2/2006 | Perret, Jr. |
| 6,997,709 B2 * | 2/2006 | Kangasniemi ........... A61C 3/00 433/147 |
| 7,357,789 B2 | 4/2008 | Bills |
| 7,662,188 B2 | 2/2010 | Yamada |
| 8,308,727 B2 | 11/2012 | Hernandez et al. |
| 8,419,737 B2 | 4/2013 | Yamada |
| 8,968,323 B2 | 3/2015 | McKay |
| 9,242,779 B1 | 1/2016 | Schildcrout |
| 2002/0151769 A1 | 10/2002 | Kim |
| 2003/0032925 A1 | 2/2003 | Stone |
| 2004/0068234 A1 | 4/2004 | Martin et al. |
| 2004/0111066 A1 | 6/2004 | Prais et al. |
| 2007/0031788 A1 | 2/2007 | Chao |
| 2008/0161846 A1 * | 7/2008 | Yamada ........... A61B 17/32070 606/190 |
| 2011/0183287 A1 | 7/2011 | Lee |
| 2011/0183289 A1 | 7/2011 | Lee |
| 2011/0230921 A1 | 9/2011 | Yamada |
| 2012/0330368 A1 | 12/2012 | Dunn |
| 2014/0234798 A1 | 8/2014 | Lim |
| 2015/0054195 A1 | 2/2015 | Greyf |

FOREIGN PATENT DOCUMENTS

| | | |
|---|---|---|
| WO | WO 2015/037838 A1 | 3/2015 |
| WO | WO2015037838 A1 | 3/2015 |

OTHER PUBLICATIONS

Oscar Hasson, DDS et al.; "Augmentation of deficient lateral alveolar ridge using the subperiosteal tunneling dissection approach"; Kaplan Medical Center; Oral Surg Oral Med Oral Pathol Oral Radiol Endod 2007, vol. 103, No. 3, e14-e19.

Efraim Kfir, DDS, et al.; "Minimally Invasive Guided Bone Regeneration"; Journal of Oral Implantology, vol. XXXIII, No. Four, 205-210, 2007.

Marc 1. Nevins, DMD, MMSc et al.; "Minimally Invasive Alveolar Ridge Augmentation Procedure (Tunneling Technique) Using rhPDGF-BB in Combination with Three Matrices A case Series", The International journal of Periodontics & Restorative Dentistry, vol. 29, No. 4, 370-385, 2009, Quintessence Publishing Co. Inc.

Feng Xuan, MD, et al.; "Vertical Ridge Augmentation Using Xenogenous Bone Blocks: A Comparison Between the Flap and Tunneling Procedures"; 2014 American Association of Oral and Maxillofacial Surgeons; J Oral Maxillofac Surg 72:1660-1670, 2014.

John N. Kent, DDS, et al.; "Alveolar Ridge Augmentation Using Nonresorbable Hydroxylapatite with or without Autogenous Cancellous Bone"; J. Oral Maxillofac Surg, 41:629-642; 1983.

Carlo Mazzocco, MD, DDS, et al.; "The Tunnel Technique: A Different Approach to Block Grafting Procedures"; The International Journal of Periodontics & Restorative Dentistry; vol. 28, pp. 44-53, No. 1, 2008; Quintessence Publishing Co, Inc., © 2008.

Ernesto A. Lee, DMD, et al.; "Lingualized Flapless Implant Placement into Fresh Extraction Sockets Preserves Buccal Aveolar Bone: A Cone Beam Computed Tomography Study"; The International Journal of Periodontics & Restorative Dentistry; vol. 34, pp. 60-68, No. 1, 2014; Quintessence Publishing Co, Inc. © 2014.

Marc I. Nevins, DMD, MMSc et al.; "Minimally Invasive Alveolar Ridge Augmentation Procedure (Tunneling Technique) Using rhPDGF-BB in Combination with Three Matrices A case Series", The International journal of Periodontics & Restorative Dentistry, vol. 29, No. 4, 370-385, 2009, Quintessence Publishing Co. Inc.

* cited by examiner

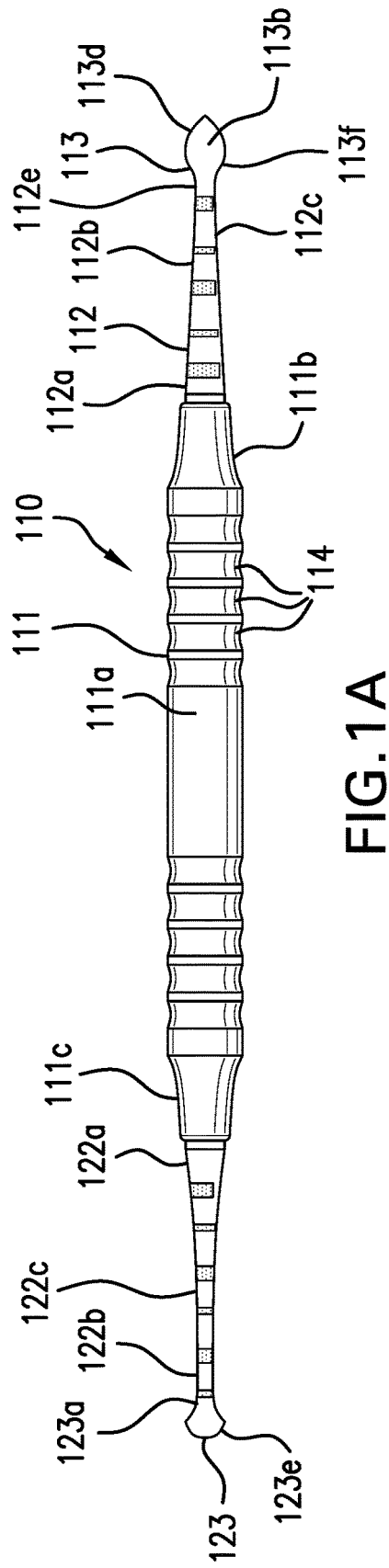
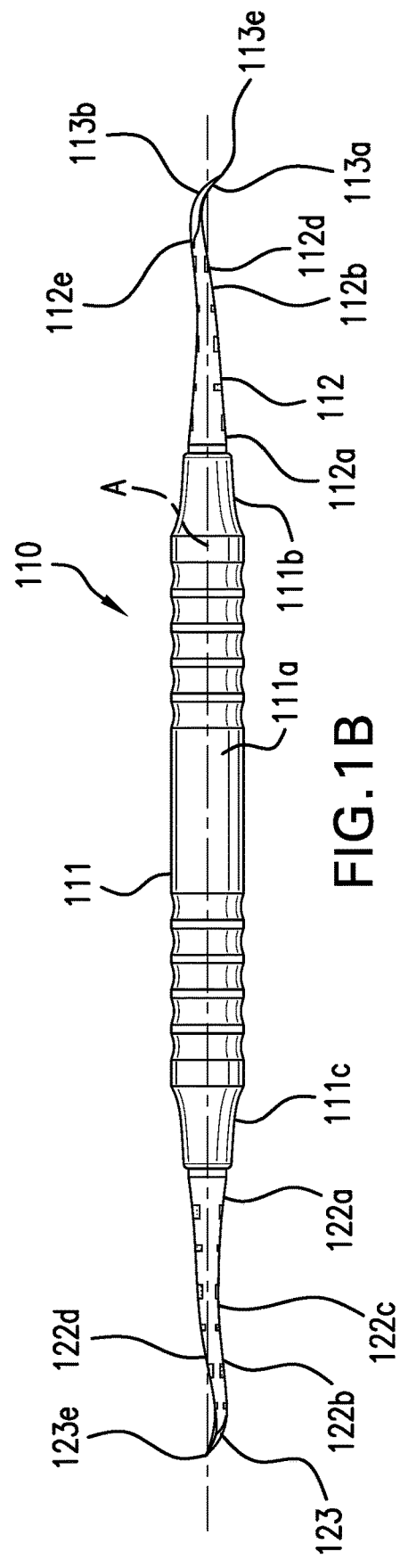
FIG. 1A
FIG. 1B

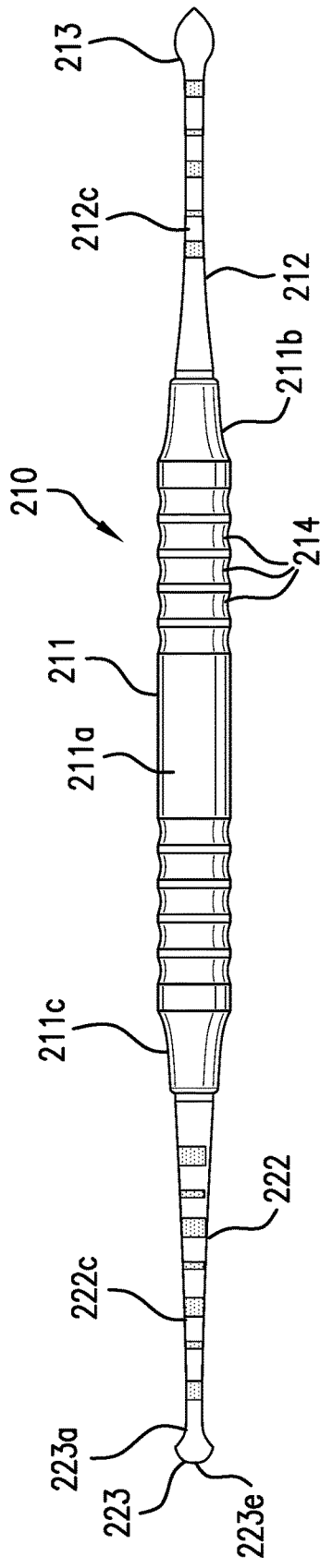
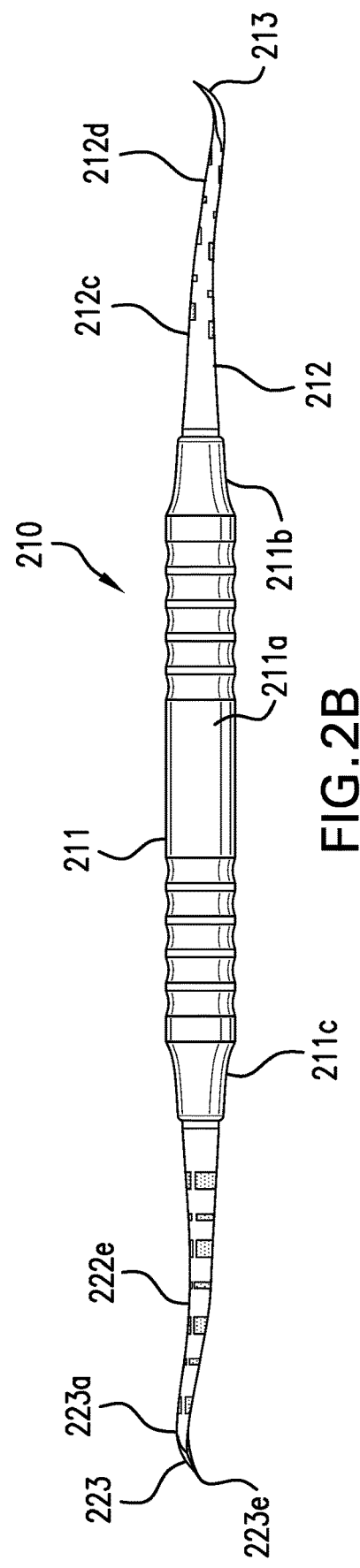
FIG.2A
FIG.2B

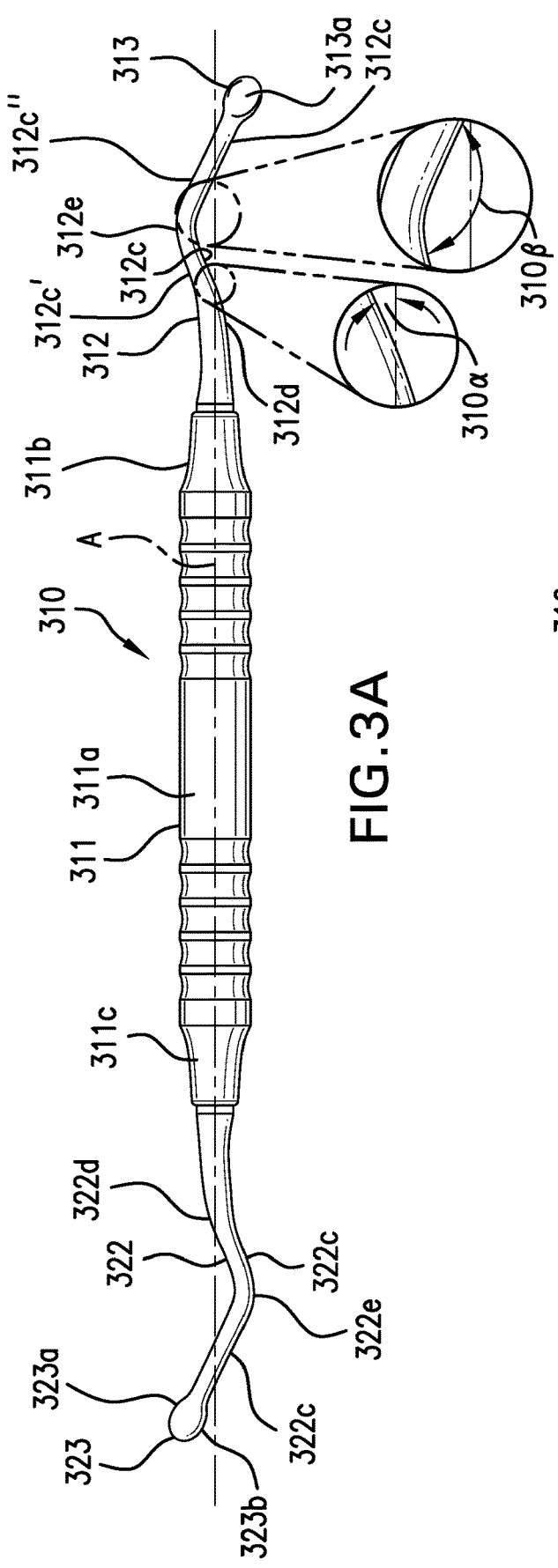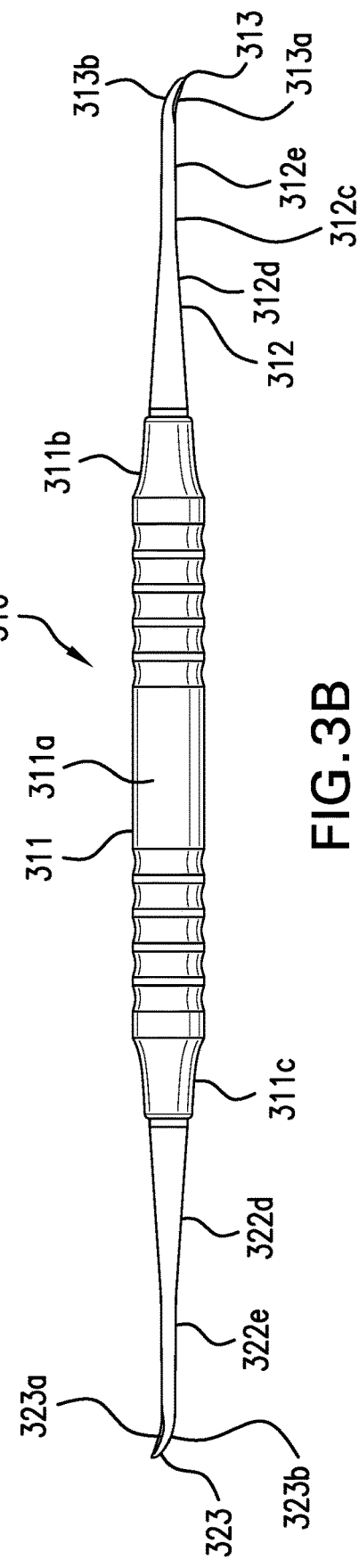

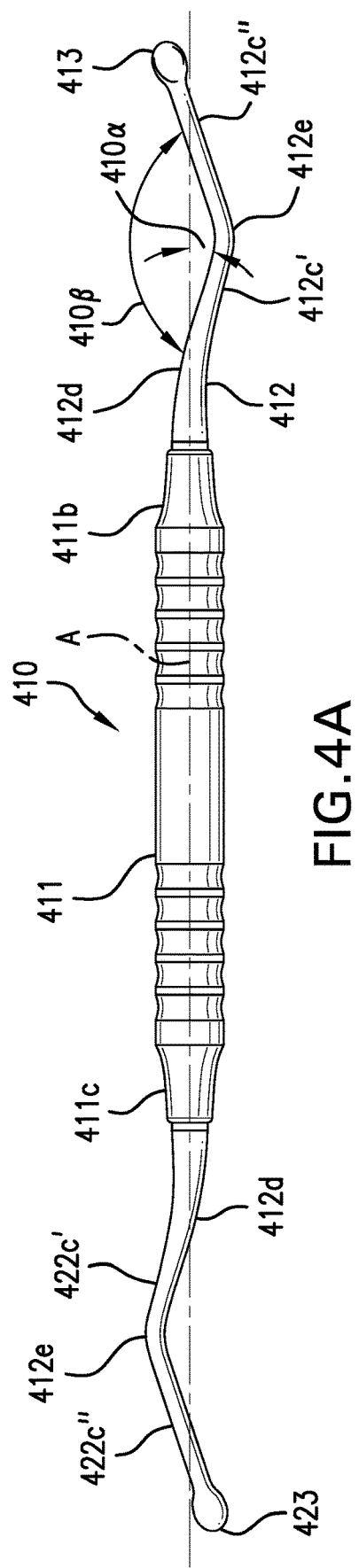
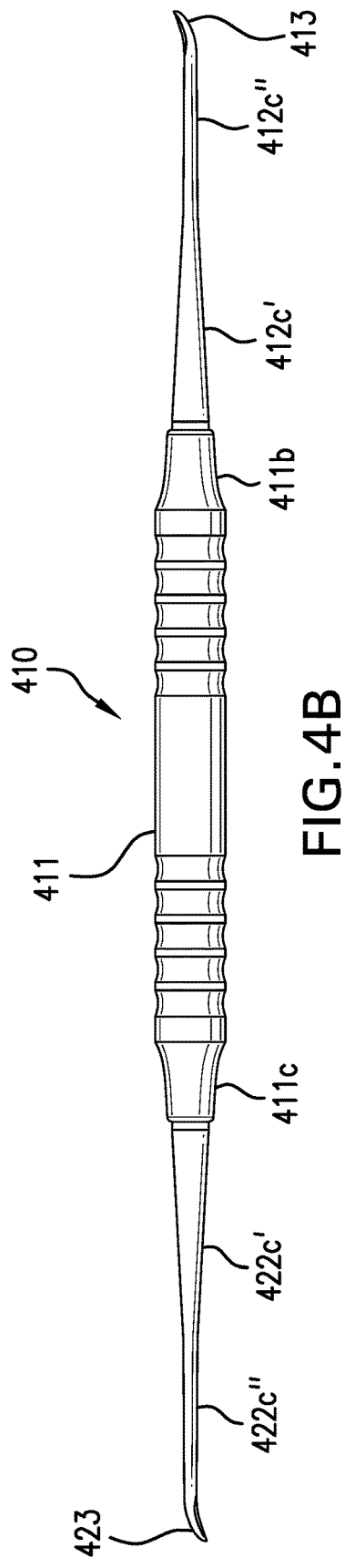
FIG. 4A
FIG. 4B

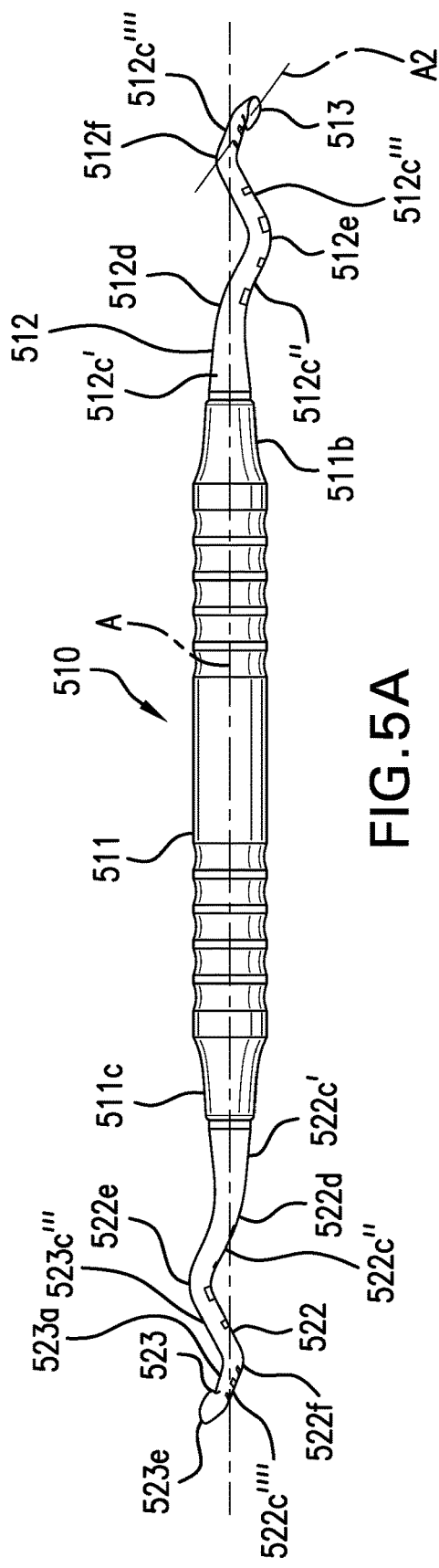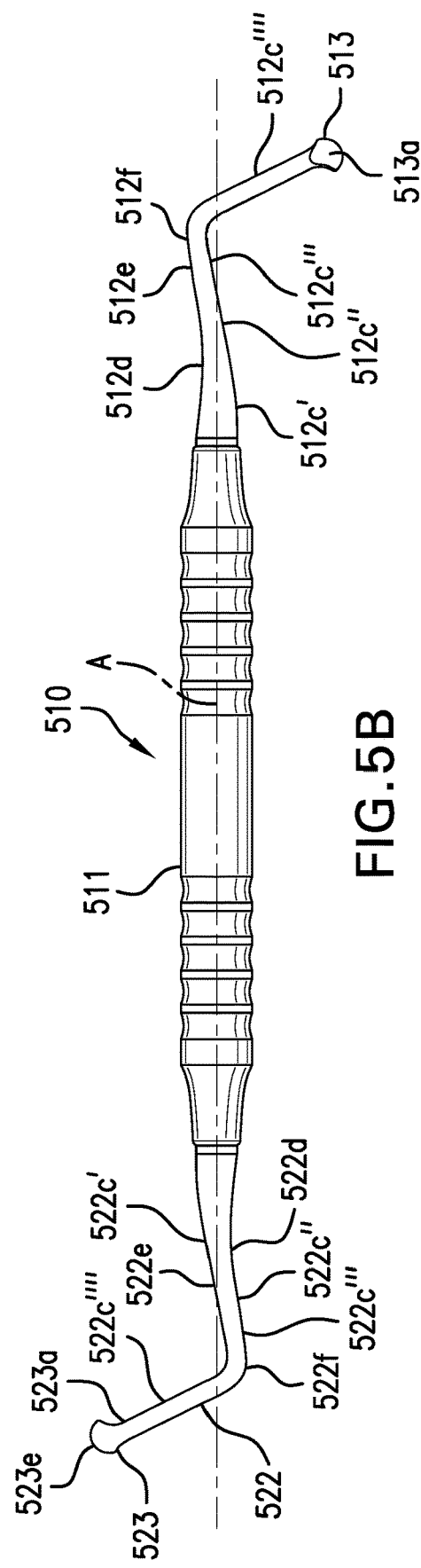

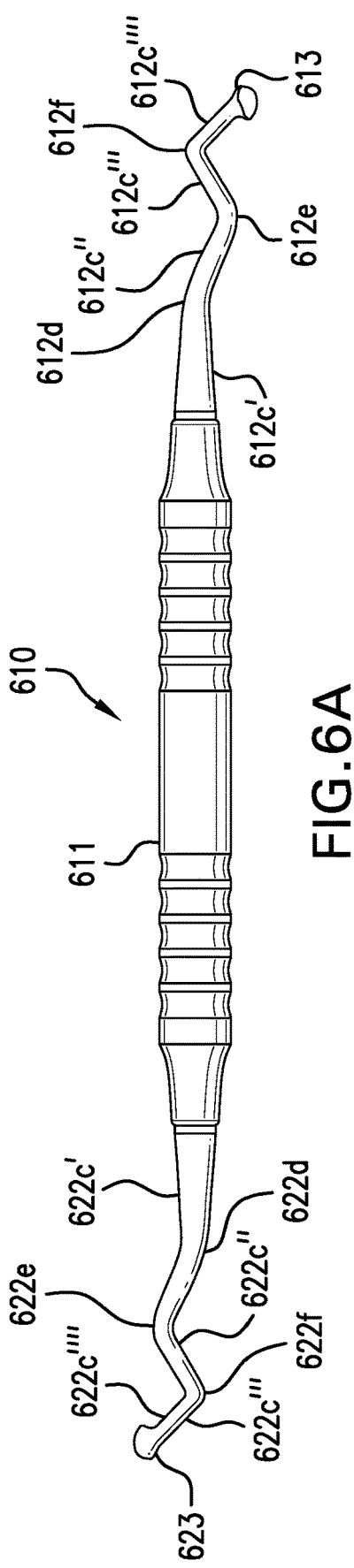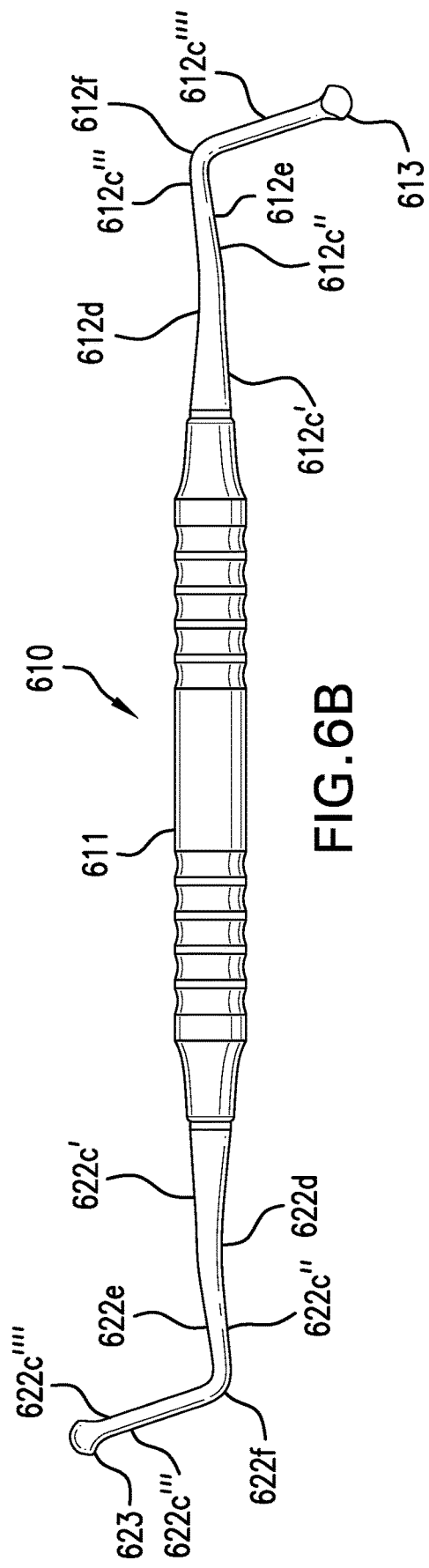
FIG.6A
FIG.6B

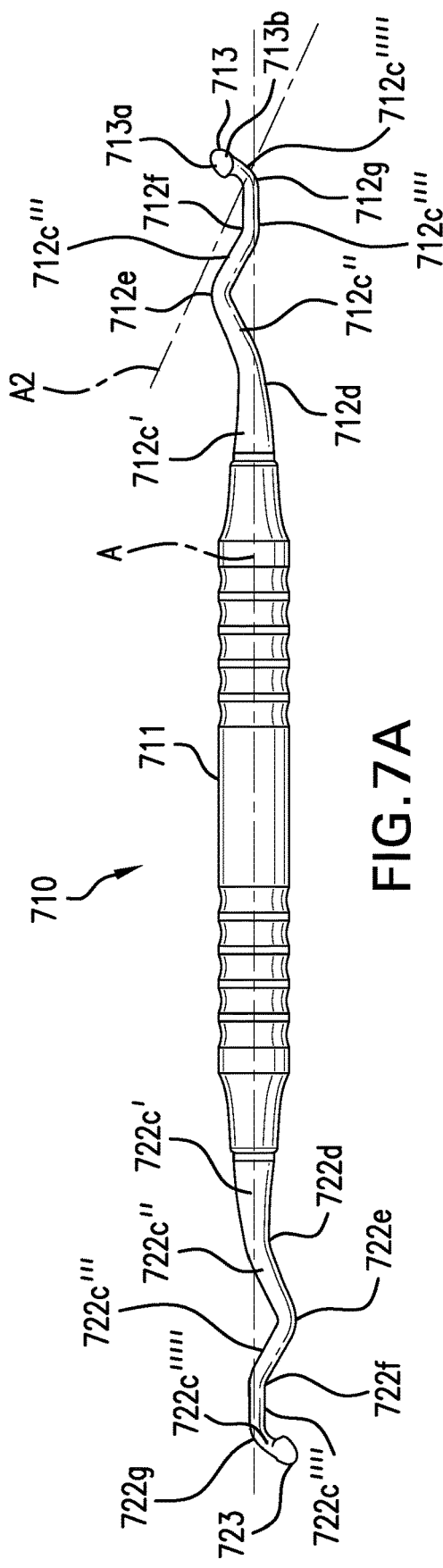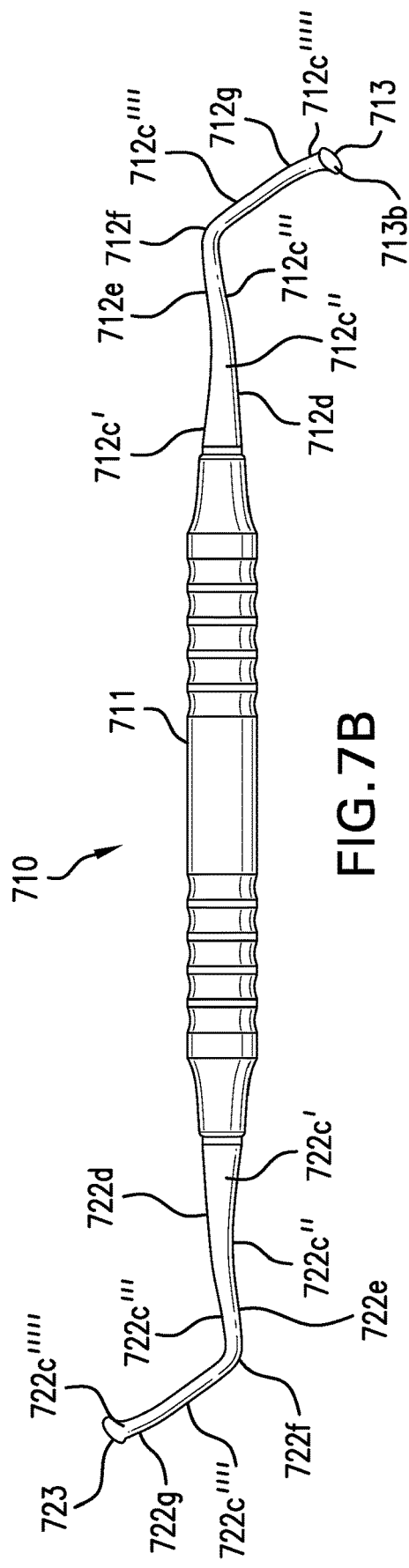

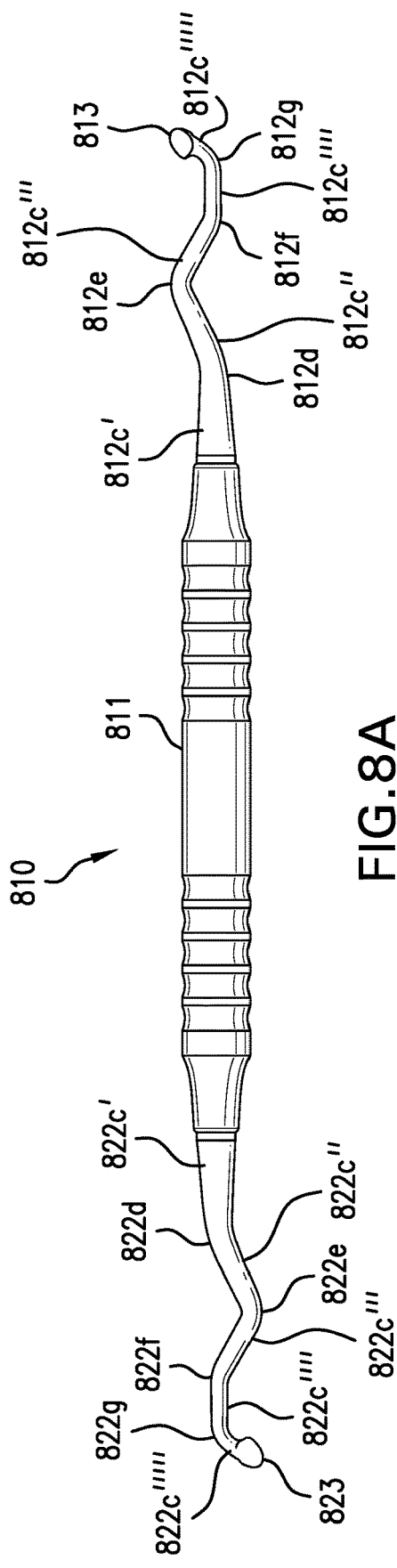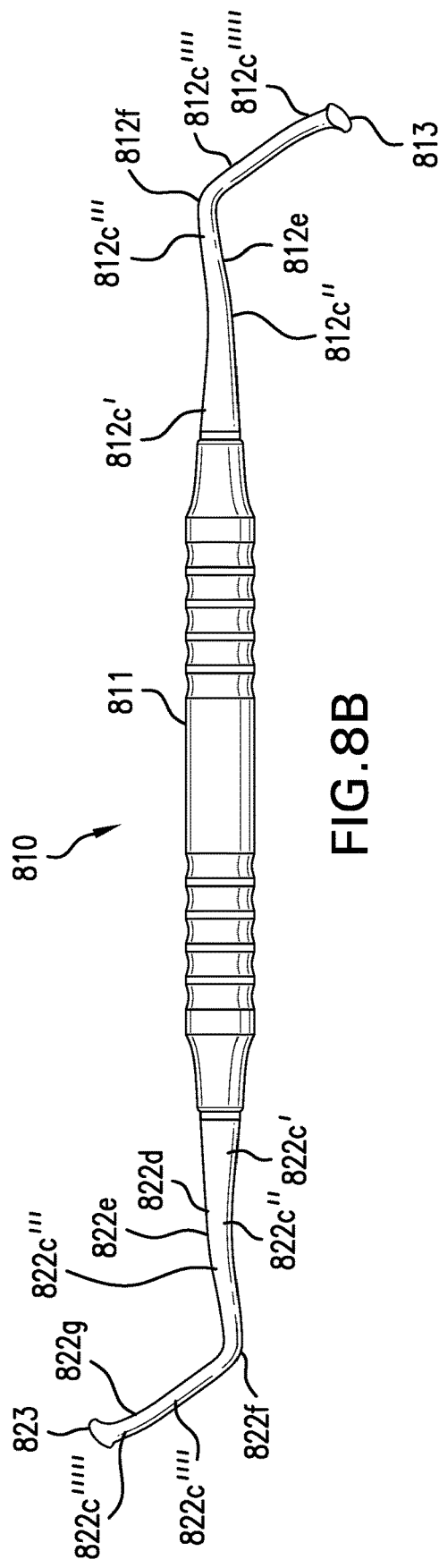

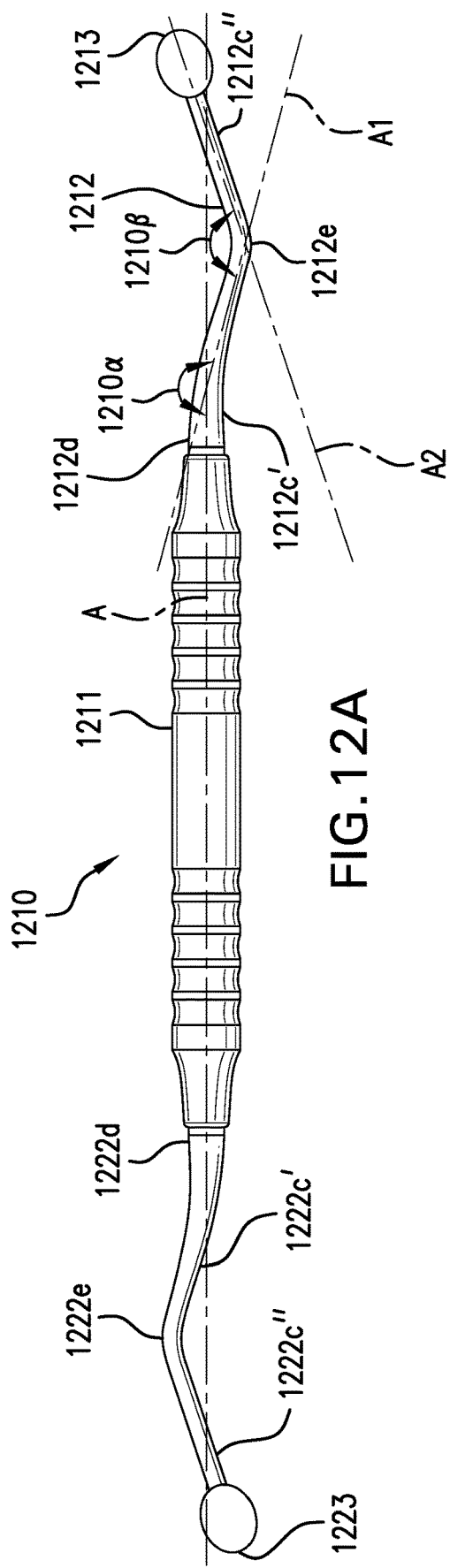
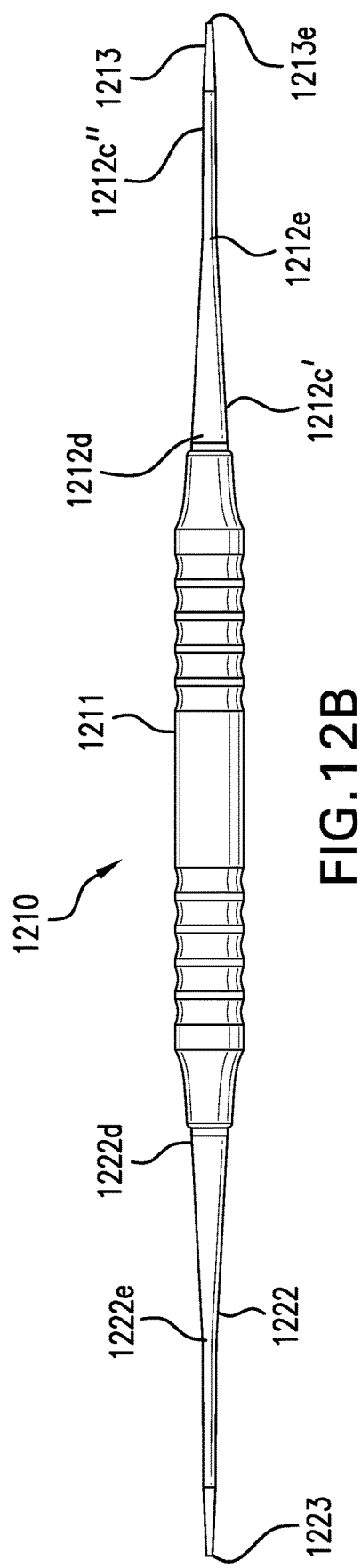
FIG. 12A
FIG. 12B

DEVICES FOR CONDUCTING SUBPERIOSTEAL MINIMALLY INVASIVE AESTHETIC JAW BONE GRAFTING AUGMENTATION AND THEIR USE

CROSS-REFERENCE TO RELATED APPLICATIONS

This patent application claims the benefit under 35 U.S.C. 119 and 35 U.S.C. 120 of International patent application Serial No. PCT/US17/25478, filed Mar. 31, 2017, and U.S. provisional application Ser. No. 62/316,140, filed Mar. 31, 2016, each entitled "Method, Devices And Articles For Conducting Subperiosteal Minimally Invasive Aesthetic Jaw Bone Grafting Augmentation", the complete contents of which are herein incorporated by reference.

FIELD OF THE INVENTION

The present invention relates to instruments and devices for minimally invasive reconstruction of the jaw, namely bone, soft tissue, gingival papillae and the attachment apparatus whereby teeth and dental implants are attached to the jaw bone, and more particularly to instruments that are used to perform subperiosteal augmentations and reconstructions, implantable jaw bone graft substrates, and their use in carrying out procedures, such as, subperiosteal augmentations and reconstructions, implantable jaw bone graft substrates, where bone material is implanted through the mucosal tissue

BRIEF DESCRIPTION OF THE RELATED ART

The human jaw bone is the supporting structure for teeth, and may be affected by a number of conditions, including age, congenital abnormalities, medical treatments, injuries, disease and trauma. The human lower jaw bone is referred to as the mandible, and the upper jaw is known as the maxilla. In a number of instances, the mandible and maxilla may change as a person ages. Reconstructions of the mandible and maxilla are carried out to correct physiologic and pathologic conditions, to remediate an aesthetic condition or appearance, or both. Subperiosteal augmentations with biomaterials to reconstruct the jaw bone may be used in individuals that have a shallow jaw bone, or jaw bone deficits due to congenital factors, disease or trauma.

Aesthetic outcomes in implant therapy are predominantly dependent on the peri-implant soft tissue architecture. Traditional bone grafting techniques include releasing incisions, papilla splitting, gingival flap elevation and manipulation to cover the augmented volume. Regardless of the degree of bone augmentation achieved, the soft tissue results often include gingival deformities leading to compromised esthetics. A relationship between the complexity of the augmentation procedure and the degree of peri-implant soft tissue deformity has been documented in the literature. Typically, the more complex procedures exhibit an increase in the level of deformity of the soft tissue. Therefore, although minimally invasive procedures have been advocated, there are certain problems encountered that have not been resolved (i.e. vertical bone augmentation, new attachment regeneration on natural teeth or implants, and gingival papillae reconstruction).

Instruments typically are provided for use with open incisions. Open incisions expose the surgical site and provide access to the subperiosteal tissue, bone and/or graft material at the surgical site to which the instrument may be guided for use at that location. However, it is advantageous to implement alternative surgical procedures where a remote incision is made, and a tunnel is surgically developed between the remote incision and the surgical site where bone graft material is to be implanted. The use of conventional instruments do not provide the capability required to maneuver through the tunnel to the surgical site, and manipulate material at the surgical site, such as tissue and bone graft material, by controlling the instrument from a location outside of the remote incision. Prior instruments are provided to directly access an exposed surgical site that is accessible from an incision at the site. The present instruments are designed to reduce trauma by minimizing the damage the tissue at the surgical site where healing is required after the deposit of the bone graft material.

A need exists for devices that are useful for carrying out subperiosteal procedures, where the surgical site is remote from an incision, is not fully exposed, and where direct access to the surgical site is not available. The present invention avoids many of the foregoing problems and permits a more effective means to minimize the invasiveness of subperiosteal augmentations and reconstructions, as well as the number of procedures, morbidity and cost for treatment applications.

SUMMARY OF THE INVENTION

Devices for use in carrying out surgical procedures are provided, and in particular, devices configured for use in carrying out subperiosteal minimally invasive aesthetic jaw bone augmentation and reconstruction. The devices are configured for use at surgical sites that are not exposed. The devices designed for use in jaw reconstruction procedures, such as mandibular and maxillary reconstructions including horizontal and vertical bone augmentations. The inventive devices or instruments may also be employed to facilitate reconstruction and regeneration of the apparatus consisting of alveolar bone, periodontal ligament and root cementum, whereby teeth and dental implants are attached to the jaw bone, and the gingival papillae also is reconstructed and/or regenerated, through the implementation of procedures that utilize the inventive devices to manipulate the tissue to accept implantable biomaterials. The devices include instruments configured with engaging portions configured as elevators and condensers that may be used to carry out reconstruction and augmentation procedures, including reconstructions of horizontal and vertical jaw defects, regeneration of the structures and apparatus whereby teeth and dental implants are attached to the jaw bone in addition to the reconstruction of gingival papillae, may be achieved with the minimally invasive method, instrumentation, and articles, including the implantable biomaterials, of the invention. Preferred embodiments of the instruments have specially configured portions that permit maneuvering to direct the instrument along a preferred path, which may be linear, non-linear of a combination of both, to generate a passageway or tunnel leading to a surgical site that is concealed within the tissue.

The devices are configured for use in carrying out alternative surgical procedures, where the device is maneuvered from a location remote of the surgical site, and preferably from outside of the patient tissue. For example, the inventive devices may be used in jaw reconstruction and augmentation procedures where a remote incision is made in the patient's mucosa. The devices may be used to make an incision and to surgically develop a tunnel in the mucosa that leads from the incision to a surgical site where bone graft material is to be implanted. The devices also may be used at the surgical site to prepare the surgical site to receive a bone graft. The devices are configured to reduce potential damage to the patient tissue by providing the capability for a user to surgically develop a tunnel in the patient mucosa by maneuvering the device in a direction desired by the user. The devices may be insertable through the tunnel to the surgical site.

The devices are configured with shanks and associated tips that are designed to allow use from outside of the surgical site and incision. The instrument may include ends that have cutting edges on a portion of or on the entire tip perimeter, to facilitate cutting of the tissue. The tips are specially configured to provide controlled intrusion into the mucosa to form a tunnel in a location directed by the instrument user. Preferred embodiments of the instruments may be used to form a tunnel in the mucosa, and are configured to elevate the periosteum as the user moves the instrument forward to develop the tunnel. The instruments may be moved forward and rearward, and may be rotated or turned to manipulate the tissue and bone graft material at the surgical site. The user of the instrument may maneuver and manipulate the instrument from a location outside of the remote incision, where the instrument tip or head, carried on the shank, is engaging implant material (bone graft material) and/or tissue to form the tunnel, or at the remotely situated surgical site. The instrument tip leading portion as well as lateral portions may be used for cutting, elevating, and/or manipulating structure, such as tissue, bone and bone graft material. The instruments provide the capability to access a concealed surgical site through a remote incision, and to form a tunnel, and access the surgical site through the tunnel tissue without the need to open the tunnel tissue on all sides. The instruments, for example, may be used to create the incision and to develop the tunnel. In addition, an instrument may be used to form the remote incision, as well as to be inserted into the incision and form the tunnel in the mucosa. In addition, the instruments may be inserted through the incision connecting to the tunnel, and may then be maneuvered through the tunnel to the surgical site. At the surgical site, an instrument may be controlled to maneuver the handle, which remains outside of the surgical site. Instrument manipulation may include rotation, as well as insertion to provide pressure from a desired angle or direction on the tissue, bone graft material, patient bone, or other fixture or structure at the surgical site. Bone graft material may be made from a mammalian or mineral material, and may be processed with one or more agents. Some examples of bone graft material include human, bovine, equine, porcine or other mammalian bone, anorganic bovine bone (e.g., non-living bone), as well as anorganic human, mammalian or mineral bone particles that are mixed with a biologic agent containing growth factors, biologic adhesive or binding substances.

Embodiments of the instruments, according to preferred configurations, provide the instruments with the capabilities for elevating the tissue or for condensing the tissue or bone structure. For example, some instruments may be configured with an elevator tip end that permits the raising of the mucosa of a surgically developed tunnel. The instrument preferably provides the tip at the end of a specially configured shank that is connected to the instrument handle. The manipulation of the handle may produce movements of the tip as a result of the shank configuration and tip geometry relative thereto. Movements may include application of an elevating effect from a direction inside the tunnel, which may be elevating relative to the bottom or a side of the tunnel, or relative to another tunnel position. The instruments may include a condensing end configured on a shaft, so that movements of the handle may effect condensing by application of a condensing force of the bone graft material. The condensing force may be applied toward the patient's existing bone (mandibular or maxillary), or relative toward another direction (such as against implanted bone graft material).

The present instruments are useful for carrying out subperiosteal procedures where the surgical site is remote from an incision, and not fully exposed to the instruments, and is concealed beneath the tissue surface. Once the jaw bone is reconstructed using the instruments to carry out minimally invasive reconstruction methods, and biomaterials are implanted, then dental implants (e.g., prosthetic teeth), may be placed to restore function. The instruments provide the capability to develop an appropriately directed tunnel within the patient tissue, to access to the remote surgical site through a tunnel, and to maneuver a deposit of bone graft material in a desired configuration or orientation so as to restore or augment the patient's existing bone. The instruments are used to carry out minimally invasive reconstruction of horizontal and vertical jaw defects, where bone replacement or augmentation promotes or produces the regeneration of the structures and apparatus whereby teeth and dental implants may be attached to the jaw bone, in addition to the reconstruction of gingival papillae.

The instruments may be used to sculpt bone graft material that is delivered to the remote surgical site (e.g., through a tunnel developed in the mucosa), which, for example, may involve bone particles, bone pastes, as well as customized granular or molded bone grafts or bone/collagen grafts in different configurations (such as graft molds, shapes and blocks, configured in different designs, compositions and dimensions). For example, the instrument configured with a condensing tip may be used to manipulate the bone graft material to form a desired position and/or orientation at the surgical site, and in other areas where manipulation of the bone material may be required (the tunnel).

The inventive instruments preferably are configured to produce elevating and condensing effects in the bone graft material and tissue, and may be used to carry out surgical procedures that include making an incision, which may be remote of the surgical site, developing a tunnel in a location in the tissue (below the periosteum) to form a passageway from the remote incision to the surgical site. The instruments also may be used to configure the surgical site to receive bone graft material. The instruments are specifically configured for use in forming a subperiosteal pouch at the surgical site by maneuvering the instrument to elevate the periosteum of the surgical site forming a pouch that will house and confine a graft. The instruments may be used to manipulate the tissue to form a subperiosteal pouch having a suitable configuration (such as the size and shape) to house a bone or bone/collagen graft that is to be located and installed at the site. The instruments may be used to manipulate the tissue to configure the pouch so that it will receive and confine the graft and maintain the graft in a desired position.

In carrying out bone augmentation or reconstruction procedures, the instruments may be used to manipulate bone graft material that is delivered to a surgical site (by a carrier). This may be done by condensing and adapting the graft material to achieve the degree of bone augmentation desired.

According to preferred embodiments, the instruments are configured with an elevator, condenser or spatula like tip, to carry out condensing of the bone material. Instruments according to embodiments of the invention may be provided having a holding area and double or single ends, on which an engaging element, such as, a condensing element or elevating element is provided. The condensing element or tip preferably is connected to a shaft or shank which connects with the instrument handle. The instrument is configured so that it may be used to provide maneuverability of the tip, such as a condensing element (which may be provided at each end thereof), so that the condensing element may be inserted into the remote incision and maneuvered through the tunnel and at the surgical site where the bone graft material (such as bone particles, bone paste, or bone articles) is positioned. The condenser has a configuration that permits manipulation using the instrument handle so that the condenser tip may pack the bone graft into the site. Other instruments may be configured with tips that may be maneuvered to mold the bone material into an appropriate shape.

Upon completion of the installation of the bone graft and condensation and adaptation in place at the site, or upon the completion of a step that requires the use of a different one of the instruments, the instrument is removed by withdrawing it from the surgical site, which must be done by retracting the instrument from the tunnel. According to some embodiments, the instruments may be configured to provide one or more rounded or non-incisive structures that engages the tissue and raises it away from the sharp or cutting edges of the instrument tip. The user may retract the instrument from the tissue, for example, when an instrument is being withdrawn from a tunnel and minimize the tendency for undesired cutting. Since the instrument movement may be maneuvered at different angles, according to some preferred embodiments, some peripheral, upper or lower edges of the instrument shank or tip may be softened or rounded to minimize or prevent undesirable damage to the tissue surrounding the tunnel passageway.

The instruments are configured to be used to carry out a procedure at a surgical site remote from an incision into which the instrument is inserted, so that upon completion of a procedure, the incision may be closed, preferably by suturing or by utilizing another suitable technique.

The present devices are designed to minimize or eliminate potential peri-implant soft tissue disfigurement. The devices and their use also provide a way to achieve consistency in horizontal and vertical augmentation of the jaw. The devices are designed to be utilized to implement procedures without losses to bone volume, and preferably, are also designed to permit less invasive techniques for providing bone volume that traditionally was achievable only with flap based or open surgical techniques (that involve direct placement of a tool at the surgical site, as opposed to through a tunnel). The devices improve predictability, and may reduce the need for the number of procedures, morbidity as well as costs.

According to preferred embodiments, the inventive instruments may be used to carry out restorations and augmentations, including, for example, vertical augmentation applications involving the jaw, which may be performed at both, mandibular and maxillary locations. The devices may be utilized to provide subperiosteal augmentation of the jaw without the need for the use of a membrane, such as a cell-occlusive membrane or space maintaining membrane, and without the step of installing the membrane. The devices also may be used to facilitate jaw bone augmentation methods that are carried out without the use of tenting screws or other space maintaining devices such as a titanium mesh and titanium reinforced membranes.

According to some preferred embodiments, the instruments are configured as a tunneling instrument that may be utilized to make the incision, develop the tunnel, and operate at the active site by forming a pocket for the graft and carrier. The tunneling instrument may be formed with a cutting portion that is disposed on a maneuverable arm that permits the tunnel formation by maneuvering the instrument arm and cutting portion through the tissue. The tunneling instrument may be configured as an elevator that may include a specially designed cutting portion at the tip to facilitate the separation of an intact periosteum layer. For example, according to some embodiments, the tunneling instrument may be configured for use in forming a subperiosteal pouch. According to preferred embodiments, the instrument may include one or more mechanisms that may be utilized to maneuver or manipulate the periosteum to create the pouch.

According to some preferred embodiments, the instrumentation may be provided in the form of a kit or separate kits which includes the components and mechanisms that may be utilized for carrying out the method. According to some preferred embodiments, the instrumentation is provided as a kit or separate kits which may be adapted to pre-existing instruments, and/or steering and viewing devices. According to some other devices, the instrumentation may be a complete kit which includes one or more displays, mechanisms for steering and moving the cutting and grasping elements of the instruments.

The instruments preferably are constructed to facilitate the pouch formation in a subperiosteal augmentation or restoration by enabling the user to manipulate the instrument to elevate the subperiosteal tunnel. The pouch is created to house and confine a graft, and the instruments may be used to configure the pouch within the periosteum, e.g., the dense layer of vascular connective tissue surrounding the mandible and/or maxilla. The instruments may be used to elevate the tunnel preferably at the location where the bone graft is to be installed in order to prepare the site for the reception of the grafting material that is to be delivered to the location (e.g., bone graft granules, paste, or a prefabricated bone graft).

The present devices may be used for jaw augmentation and restoration procedures and in particular, to carry out procedures that are designed to be less invasive than prior methods. According to preferred embodiments, the instruments may be used to carry out subperiosteal augmentations and reconstructions in the maxillary anterior region with minimal or no risk of disfigurement to the patient.

BRIEF DESCRIPTION OF THE DRAWING FIGURES

FIG. 1A is a top plan view of an exemplary embodiment of device according to the invention configured as an elevator.

FIG. 1B is a right side elevation view of the device of FIG. 1A.

FIG. 2A is a top plan view of an alternate embodiment of a device according to the invention configured as an elevator, being similar to the device of FIG. 1A, having a longer reach.

FIG. 2B is a right side elevation view of the device of FIG. 2A.

FIG. 3A is a top plan view of a third alternate embodiment of device according to the invention configured as an elevator.

FIG. 3B is a right side elevation view of the device of FIG. 3A.

FIG. 4A is a top plan view of a fourth alternate embodiment of device according to the invention configured as an elevator, being similar to the device of FIG. 3A, having a longer reach.

FIG. 4B is a right side elevation view of the device of FIG. 4A.

FIG. 5A is a top plan view of a fifth alternate embodiment of a device according to the invention configured as an elevator.

FIG. 5B is a right side elevation view of the device of FIG. 5A.

FIG. 6A is a top plan view of a sixth alternate embodiment of a device according to the invention configured as an elevator, being similar to the device of FIG. 5A, having a longer reach.

FIG. 6B is a right side elevation view of the device of FIG. 6A.

FIG. 7A is a top plan view of a seventh alternate embodiment of device according to the invention configured as an elevator.

FIG. 7B is a right side elevation view of the device of FIG. 7A.

FIG. 8A is a top plan view of an eighth alternate embodiment of device according to the invention configured as an elevator, being similar to the device of FIG. 7A, having a longer reach.

FIG. 8B is a right side elevation view of the device of FIG. 8A.

FIG. 12A is a top plan view of a twelfth alternate embodiment of device according to the invention configured as a compactor, being similar to the device of FIG. 11A, having a longer reach.

FIG. 12B is a right side elevation view of the device of FIG. 12A.

DETAILED DESCRIPTION OF THE PREFERRED EMBODIMENTS

Figure 1C:
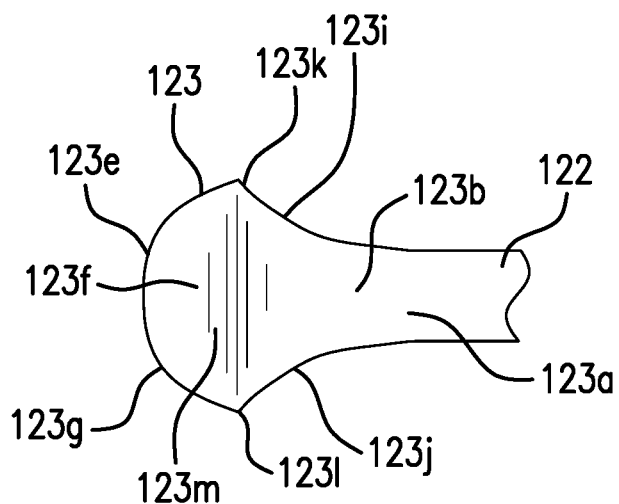
FIG. 1C is an enlarged partial view of the device of FIG. 1A, showing the tip end.
Figure 1D:
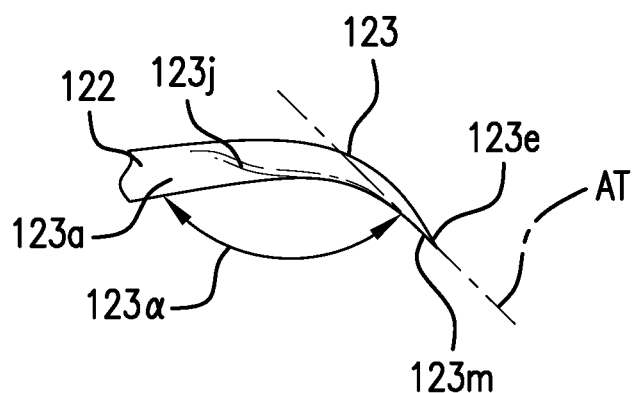
FIG. 1D is an enlarged partial view of the device of FIG. 1A, shown rotated about 90 degrees from the position in FIG. 1B.

FIGS. 1A-1D are views of an exemplary embodiment of an elevator 111 according to the invention, FIG. 1A showing a top plan view, FIG. 1B showing a side elevation view, and FIGS. 1C and 1D showing respective end views of the element of the respective instrument end.

Referring to FIGS. 1A to 1D, what is illustrated is a device comprising a dental surgical instrument 110 for use in carrying out a subperiosteal augmentation or reconstruction procedure involving the creation of an incision, insertion of the instrument 110 through an incision remotely situated from a surgical site where bone is to be implanted, and the maneuvering of the instrument 110 through the tissue to develop a tunnel within the periosteum that leads to the surgical site. The instrument 110 includes cutting edges provided on the tip 113, and may be used to prepare the surgical site to receive bone graft material.

The dental instrument 110 is shown configured as an elevator. The dental instrument 110 includes a handle 111, an elongate shank 112 connected to the handle 111 at the proximal end 112a of the shank 112 and being shown extending from the barrel shaped handle body 111a. A tip 113 is provided at the distal end 112e of the elongate shank 112. The handle 111 may be provided with a surface treatment or structure to facilitate holding and grasping of the instrument, some examples of which include knurlings, flutings or other elements to enhance gripping of the instrument. In the exemplary embodiment illustrated, the device 110 is shown having a knurled surface structure, such as the bands 114, provided on the exterior of the cylindrical or barrel shaped handle body 111a to facilitate holding and grasping the instrument 110 (e.g., from a package, tray and/or during use). The barrel shaped handle body 111a includes a reduced diameter portion 111b provided at the handle end where the shank 112 is shown connecting with the handle 111. According to some embodiments, the shank 112 preferably may be elongated to span inside the handle 111, and preferably is secured within the handle 111. According to some embodiments, the shank 112 may be coextensive with a portion of the handle 111, or all of the handle 111, and according to embodiments, may span through the handle 111 to provide a second shank 122 extending from the opposite side of the handle 111. For example, the first shank 112 and second shank 122 may be separate, or may be formed from a single elongated structure. According to some alternate embodiments, the first shank 112 or the second shank 122, or both, may be formed with the handle 111, as a single piece. Alternatively, the instrument 110, although shown having a shank 112, 122 at each end thereof, may be constructed with a single shank (112, or 122), and may be provided as two separate instruments.

The shank 112 has a larger diameter portion 112a closest to where the shank 112 joins the handle 111. The shank diameter is shown tapering to a smaller diameter 112b, moving from the handle 111 to the distal end of the shank 112 where the tip 113 is located. The tip 113 is provided on the distal end 112e of the shank 112 and is shown at the end of the shank shaft 112c. Referring to FIG. 1B, as seen from the side view, the shank 112 has a slight gentle curvature 112d to the shank shaft 112c. As shown in the exemplary embodiment of the instrument 110, the shank shaft 112c is free from sharp angles.

In the instrument embodiment illustrated in FIGS. 1A-1D, the first tip 113 at the shank distal end 112e is shown having a triangular shape. The tip 113 extends at an angle to the central axis A of the shank shaft 112c, as shown in the side view in FIG. 1B. Preferably, the angular disposition of the tip relative to the shank shaft 112c central axis A is from about 20 to 70 degrees, and more preferably from between about 40 to 60 degrees. The tip preferably has a concave or flat bottom surface 113a (FIG. 1B) and has a convex top surface 113b (FIG. 1A). According to some preferred embodiments, the shank shaft 112c, as shown in the side view of FIG. 1B, curves above the central axis A and returns below the central axis A. Preferably the tip 113 is provided to reside below the central axis A when the device 110 is oriented as shown in the side view of FIG. 1B. The tip 113 is configured with curved edges, which preferably are sharp along the perimeter and comprise a cutting edge or curved cutting periphery designed to be used for cutting when manipulating the tool (through tissue or into bone). The tip 113 has a proximal edge 113f that meets the distal end 112e of the shank shaft 112c, which preferably may be rounded and smooth. According to a preferred configuration, the top plan view of FIG. 1A shows the tip tapering from a narrow width where the tip joins the shank shaft 112c, widening toward a location 113d just before the tip end 113e. According to some preferred embodiments, the widest portion of the tip 113 is located about two thirds of the distance from the start of the tip 113 to the tip end 113e, which in the embodiment illustrated is represented by the tip location 113d. The tip 113 is shown having a preferred shape which is triangular, and preferably a rounded or curved triangle, such as a tear drop shape.

The shank 112 preferably is provided having a suitable length that provides sufficient penetration depth to pass through a subperiosteal tunnel and reach the intended surgical site. According to some preferred embodiments, the shank 112 may have lengths between about 30 to 85 mm, and more preferably from between about 35 to about 65 mm. According to an exemplary embodiment, the instrument 110 may be configured having a shank radial dimension from about 1 mm to about 2 mm, with the large diameter shank portion (112a) being about 3 to 8 mm in diameter, and the narrower shank portion (112b) diameter, where the shank shaft 112c joins with the tip 113, being about 1 to 5 mm, and preferably about 2.5 mm. The bottom tip surface concavity 113a preferably has a radius of curvature and the upper or convex top surface 113b preferably has a radius of curvature, examples of which are illustrated in the exemplary embodiment shown in FIGS. 1A-1D.

Although the instrument 110 may be constructed with a shank 112 having a length suitable to reach the intended surgical site through the incision and the length of the tunnel, according to some embodiments, the shank 112 may be from about 30 to 60 mm. The instrument 110 may be constructed in different sizes to provide shank lengths that are longer or shorter. The medical personnel user may select an instrument based on the length required for the procedure. Referring to FIGS. 1A and 1B, the shank 112 may be provided having a length of from about 30 to 60 mm, and according to one preferred embodiment, the shank length is about 35 mm. The tip 113 preferably may be provided with a suitable diameter or width for use, and according to a preferred embodiment, may have a width at its widest dimension to be about 4.5 mm.

The outer surface of the shank 112 preferably may include a series of evenly spaced markings which may be visibly provided thereon to mark the depth from the tip end 113e to the marking indicia of the shank 112, so as to provide a depth indication to the user when the instrument 110 is inserted in a subperiosteal tunnel, as to the instrument penetration depth.

The elevator instrument 110 preferably provides the specially configured tip 113 at its leading end for elevating the mucosal tissue along the incision, which preferably involves elevating the mucosal tissue along the tunnel leading to the surgical site or pouch, the tunnel being the pathway through which the bone graft material will be delivered to the surgical site (which is the pouch to receive the bone graft material). The tip may be presented to the tissue to form an incision using the sharp peripheral tip edge. The instrument tip 113 may be further guided through the tissue by the user, so that the instrument 110 is moved along with the tip and shank entering the tissue, and elevating the tissue as the user maneuvers and manipulates the instrument to form a tunnel in the periosteum.

As shown in the figures, the tip 113 preferably is offset from the instrument 110 central axis A (see FIG. 1B) to facilitate elevation of the mucosal tissue bordering the tunnel. The shank 112 preferably is smooth and has rounded edges, and may be cylindrical or radial in configuration so as to further facilitate insertion and maneuvering of the shank 112 through the mucosal tissue.

According to preferred embodiments, the shank 112 may be configured having a larger cross-sectional diameter at the shank 112 proximal end 112a (the shank portion nearest to the handle 111), which may taper or narrow over the length of the shank 112 to the tip 113, or, alternatively, which may taper to a location along the shank 112, proximal from the tip 113.

According to preferred embodiments, the instruments may be constructed with two usable ends. The instrument 110 shown in the exemplary embodiment includes a second shank 122 provided at the instrument end opposite the first shank 112. The second shank 122 has a tip 123, and in the embodiment illustrated, has a configuration that is different from the first tip 113 on the opposite end. The second tip 123 may be formed on the end of the second shank 122, and the second shank 122 may be the same as the first shank 112 in terms of dimensions and configurations, or, may be different. Preferably, the second shank 122 is configured to have suitable dimensions, like the first shank 112, so as to be useful to develop a tunnel within the periosteum and maneuver therein. In the exemplary embodiment depicted, the second shank 122 extends from the barrel shaped handle body 111a in the direction opposite the extension of the first shank 112. The tip 123 is provided at the distal end of the elongate second shank 122. The second shank 122, similar to the first shank 112, is shown having a larger diameter portion 122a closest to where the second shank 122 joins the handle 111, preferably, at the handle second reduced diameter portion 111c (provided at the handle end opposite the first reduced diameter portion 111b). The diameter of the second shank 122 is shown tapering to a smaller diameter 122b, moving from the handle 111 to the distal end of the shank 122 where the tip 123 is located. The tip 123 is provided on the shank distal end 122e and is shown at the end of the shank shaft 122c. Referring to FIG. 1B, as seen from the side view, the second shank 122 is provided with a slight gentle curvature 122d to the shank shaft 122c, and, preferably, is free from sharp angles.

In the embodiment illustrated, the second tip 123 at the second end of the handle 111 is shown configured as a fan shape, where the proximal tip portion 123a joining with the shank shaft 122b is configured as a narrower portion, and, from that point distally, the tip 123 widens, fanning out, so that the wider portion of the tip 123 is located at a point along the tip axis that is between the distal end of the tip 123e and the proximal end 123a that joins with the shank 122. As shown best in FIG. 1C, the second tip 123 has a proximal tip portion 123b and a distal tip portion 123c. For example, the enlarged view of the tip 123 is shown in FIG.

1C, and illustrates the tip having a wide portion formed by a diameter, and a leading portion or distal portion 123c with an arcuate profile 123f. The arcuate profile 123f comprises a sharp edge 123g for cutting (e.g., soft and hard tissue, and bone) which, in the exemplary embodiment illustrated, may be defined by a radius. For example, according to some preferred embodiments, the diameter may form a width of the fan shaped tip 123, and may form the widest point, and the leading or distal portion 123c may be formed as a divergent body, such as for example, having a semi-circular, arcuate, curved partial oval, or partial elliptical shape, and in particular, having a periphery of such a shape. The proximal portion 123b of the tip 123, located between the wide width (where, in the embodiment illustrated, edges 123i, 123k are located) and the shank 122, preferably may be inwardly tapered, and preferably may be configured with inwardly directed curved edges, such as the curved edges 123i, 123j, which are concave relative to a central axis of the tip 123. Referring to FIG. 1D, the tip 123 also is illustrated having a preferred bend or angle 123α, which preferably is relative to the central axis A of the portion of the shank 122c to which the tip 123 joins. The angle 123α is formed by the central axis A of the shank portion 122c and the central axis of the tip AT, and is shown measured relative to the upper surface 123m. Preferably, the angle 123α is less than 180 degrees, and more preferably is between about 120 to 170 degrees. The tip 123 provides the instrument 110 with the capability to cut through tissue and bone by maneuvering the instrument 110, via manipulation of the handle 111 (e.g., forward, axially right or left, or angularly). The instrument 110, for example, may be used to construct a tunnel in the mucosal tissue that leads to the surgical site within the periosteum where implantable bone graft material will be deposited. The instrument tip 123 facilitates moving the instrument 110 in a forward direction to move the shank forward in the structure, such as tissue, and directing the tunnel formation along a desired path, which may be linear or non-linear. For example, the instrument 110 may be used to develop a tunnel within the periosteum of the tissue, and the divergent end of the tip 123 is configured to elevate the tunnel when forming the tunnel so as to facilitate directing the location where the tunnel will be developed. The instrument tip 123 also includes edges 123k, 123l on opposite ends where the arcuate fan like portion 123f, or distal portion of the tip 123, meets with the proximal arcuate portions 123i, 123j, respectively. The edges 123k, 123l facilitate manipulations of the instrument 110 to direct cutting in a desired path, such as occlusal or lingual direction. The edges 123k, 123l preferably may be sharp corners, or alternately may be curved edges, and sharp corners, or alternative curved edges, may be provided with a cutting periphery. The proximal arcuate portions 123i, 123j, respectively, preferably are not required but could be provided with a cutting periphery. For example, the instrument 110 may be used to develop a tunnel in the mucosal tissue that may be directed along a non-linear path. According to a preferred embodiment, the tip 123 has an upper surface 123m and a lower surface 123n. As shown in the exemplary embodiment, the upper surface 123m may be concave, and the lower surface 123n may be flat or preferably may be convex.

As discussed above in connection with the first shank 112, the second shank 122 may have a similar dimension or length. For example, embodiments of the instrument 110 may provide the second shank 122 having a length of from about 30 to 60 mm. According to one preferred embodiment, the shank length may be about 35 mm. The tip 123 preferably may be provided with a suitable diameter or width for use, and according to a preferred embodiment, may have a width at its widest dimension, where the fan is spread out, to be about 4.5 mm. According to some embodiments, the instrument 110 may be constructed with different tips, such as the first end tip 113 and second end tip 123 shown in the instrument 110. The tips also may be provided having the same width dimension at their widest point, such as the 4.5 mm dimension, referenced in an exemplary embodiment for the triangle or tapered first tip 113 and for the fan shaped second tip 123.

According to an alternate embodiment, as illustrated in FIGS. 2A-2B, an embodiment of an elevator instrument 210 is shown. The elevator instrument 210, in the exemplary embodiment, is similar to the instrument 110 of FIGS. 1A and 1B, except that the shank 212 is longer, and has a longer shank shaft 212c. The shank shaft 212c on the first end of the instrument 210 is longer in relation to the embodiment depicted in FIGS. 1A and 1B, so as to position the tip 213 distally further from the handle 111. According to some embodiments, the length of the shank 212 may be provided from between about 40 to 80 mm, and in an exemplary embodiment, the length of the shank 212 may be about 45 mm. The second end of the instrument 210 includes a second shank 222, which is longer than the second shank 122 of the instrument 110 shown in FIGS. 1A and 1B. The second shank 222 also may be provided having a dimension similar to the first shank 212. The embodiment of the instrument 210 is shown having shanks 212, 222 of equal length. The second end of the instrument 210 includes shank 222 that is comprised of a shank shaft 222c provided with a tip 223 at the distal end. The tip 223 is configured as a fan shape, where the proximal tip portion 223b joining with the shank shaft 222 at the proximal tip end 223a is configured as a narrower portion, and, from that point distally, the tip 223 is shown widening and fanning out, so that the wider portion of the tip 223 is the tip distal portion 223c.

The first tip 213 of the instrument 210 is shown configured having a triangular shape, being wider at the tip proximal portion 213b where the tip 213 joins the shaft 212. The tip 213 tapers and is shown converging from the proximal end 213a toward the distal portion 213c, where the tip 213e is provided having a point. According to preferred embodiments, the lateral edges 213f, 213g are sharp cutting edges that may be used to cut through soft and hard tissue as well as bone. As shown in the side view of FIG. 1B, the first tip 213 preferably is angularly bent relative to the central axis A of the first shaft 212c. In the embodiment illustrated, the first tip 213 is shown being angularly disposed relative to the shank second portion 212c", and away from the central axis A. The second shank portion 212c" is itself shown being angularly disposed relative to the first shank portion 212c', and bent away from the central axis A. According to a preferred embodiment, the shank first portion 212c' and second shank portion 212c" and bend 212d may lie in the same axial plane. The second tip 223 also may be provided with a bend 222d, similar to the bend 212d, which may be provided along the central axis A, with the shank first portion 222c' and shank second portion 222c" forming an angular relation at the bend 222d.

Referring to FIGS. 3A and 3B, an alternate embodiment of an elevator instrument 310 according to the invention is illustrated. The instrument 310 preferably is constructed having a handle 311, with a handle body 311a and a reduced diameter portion 311b, 311c, at each end thereof. The first shank 312 is shown extending from the handle body, which in this embodiment is from the handle tapered portion 311b, and terminating in a tip 313. The shank 312 is provided having two bends, including a first bend 312d, which in the top view of FIG. 3A turns to the left of, or away from, the central axis A, and a second bend 312e that bends back toward the axis A, to the right. According to a preferred embodiment, as depicted in the side view of FIG. 3B, the first shank 312, and second shank 322 have bends that lie within a plane. For example, according to an exemplary embodiment illustrated, the first bend 312d and second bend 312e bend to the left or right of the axis A (relative to the top view of FIG. 3A), but remain in the same axial plane.

The first tip 313 and second tip 323, in the instrument 310, preferably are mirror images of each other. The tip 313 is illustrated having an elliptical configuration. Preferably, the elliptical tip 313 has an elliptical length that is greater than the elliptical width, with the elliptical length spanning in the same direction as the axis of the shank shaft 312c to which the tip 313 is connected. The elliptical width of the tip 313 preferably is the widest width of the tip taken perpendicular to the shank shaft 313c. According to some embodiments, the elliptical tip 313 may form a tapered portion at its proximal end where it joins with the shank second portion 312c". The instrument 310 is configured with a second end having a second tip 323 provided at the end of the second shaft 322. The second shaft 322 is shown extending from the handle body 311a and in particular from a tapered end portion 311c. The bends in the shank 312 preferably are provided as discussed and shown in connection with the first shank 312. A first bend 322d and second bend 322e are provided, but with mirrored orientation relative to the bends of the first shank 312. The shank shaft 322c moves axially away and to the right (looking from the top view in FIG. 3A) of the axis A, and, at the second bend 322e, the shank shaft 322c moves toward the axis A, toward the left, and crosses the axis A, and then terminates at the tip 323. An elliptical tip 323 is provided at the distal end of the shank shaft 322c. According to a preferred embodiment, the second tip 323 is the same as the first tip 313, and preferably is an elliptical tip. According to some embodiments, the first tip 313 and second tip 323 are mirror images of each other. The first tip 313 is shown having a concave surface 313a on one side thereof, and preferably, has a flat surface or convex surface 313b (FIG. 3B) on the other side. The second tip 323 is shown having a flat or convex surface 323b on one side thereof, and preferably, has a concave surface on the other side 323a. According to preferred embodiments, the first bend 312d and second bend 312e form two portions of the shank shaft 312c, including a first portion 312c' and a second portion 312c". The first portion 312c' is shown shorter than the second portion 312c". According to preferred embodiments, the shank 312 at the first bend 312d is angled away from the central instrument axis A, represented by angle alpha, 310α. The shank first portion 312c' meets the shank second portion 312c" at the second bend 312e, and the shank second portion 313c" bends inwardly toward the central axis A, relative to the first portion 312c', at an angle represented by angle beta, 310β. According to a preferred embodiment, the first angle, angle alpha, 310α, that the first portion 312c' makes with the axis A is relatively smaller than the angle beta, 310β, that the first portion 312c' makes with the second portion 312c". According to a preferred embodiment, the first angle alpha (310α) is about 30 degrees, whereas the second angle beta (310β) is about 120 degrees. The angular ratio between the first angle alpha (310α) and second angle beta (310β) preferably may be about 1:4. As illustrated in FIGS. 3A and 3B, the second shaft 322 preferably is provided with angular bends similar to the bends described in connection with the first shaft 312, which preferably may be provided with similar angular relationships.

According to a preferred embodiment, an elevator 310 is constructed with the portion of the shank shaft 312c between the first bend 312d and second bend 312e being about 14 mm, and with the portion between the second bend 312e to the tip 313, and inclusive of the tip length, being about 22 mm. Similarly, the second shank 322c may be constructed with similar dimensions. Each elliptical tip 313, 323, preferably is about 5.5 mm in length, and has a width of about 4 mm.

According to alternate embodiments, the instrument 310 may be configured with a fan like tip, such as, the fan tips shown and described herein, including, for example, the tip 123 shown and described in connection with FIGS. 1A-1D. The instrument 310 may be configured with the bends and shank provided with a fan like tip at one or both ends.

An alternate embodiment of an elevator 410 is shown in FIGS. 4A and 4B. The elevator 410 is similar to the elevator to the instrument 310 of FIGS. 3A and 3B, except that each shank 312, 323 is longer, and the angles of the shank bends, the first angle alpha (410α) and second angle beta (410β) in the instrument 410 are provided to produce less of a bend. The first angle alpha (410α) of the instrument 410 is less than the corresponding angle (410α) of the instrument 310. The second angle beta (410β) of the instrument 410 is greater than the second angle beta (410β) of the instrument 310. The shank shaft first portion 412c' on the first end of the instrument 410 is longer in relation to the shank shaft first portion 312c' in the instrument 310 depicted in FIGS. 3A and 3B, as is the second shank portion 412c" which is longer than the corresponding shank second portion 312c" of the instrument 310. In the longer instrument 410, the tip 413 is distally further from the handle 411. The shank 412 is constructed to have less pronounced angular bends at the first bend 412d and second bend 412e so as to provide a maximum instrument width that includes deviations from the central axis A, on either side. According to some embodiments, the axial width or window for the instrument 310 may be the same window as for the instrument 410, with the additional shank length being accommodated by a reduction in the outward deviation of the shaft relative to the central axis A. The second instrument end includes a second tip 423 provided at the end of the second shaft 422. The second shaft 422 extends from the handle 411, and preferably from the tapered portion 411c and to where it joins the tip 423 at the distal shank end. Similar to the first shaft portion 412c' and shank second portion 412c" of the first shaft 412, the second shank shaft 422 includes a shaft first portion 422c' and shaft second portion 422c".

According to a preferred embodiment, the elevator 410 is constructed with the portion of the shank shaft 412c between the first bend 412d and second bend 412e being about 19 mm, and with the portion between the second bend 412e to the tip 413, inclusive of the tip length, being about 27 mm. Similarly, the second shank 422c may be constructed with similar dimensions. In a preferred embodiment, each elliptical tip 413, 423, preferably, is about 5.5 mm in length, and has a width of about 4 mm.

According to alternate embodiments, the instrument 410 may be configured with a fan like tip, such as, the fan tips shown and described herein, including, for example, the tip 123 shown and described in connection with FIGS. 1A-1D. The instrument 410 may be configured with the bends and shank provided with a fan like tip at one or both ends.

Referring to FIGS. 5A and 5B, an alternate embodiment of an elevator instrument 510 for use in subperiosteal augmentation procedures is shown. The instrument 510 includes a handle 511, a shank 512 extending from the handle 511, with a tip 513 at the end of the shaft 512. The shank 512 includes a plurality of shank shaft portions, which in the embodiment depicted are first through fourth shank shaft portions 512c', 512c", 512c'" and 512 c"", respectively. The shank 512 includes a plurality of bends, which from the proximal shank end to the distal shank end where the tip 513 is located, are depicted as a first bend 512d, a second bend 512e, and a third bend 512f. The first bend 512d and second bend 512e are on the same axis, which is in a plane parallel to the central axis A. The third bend 512f is provided transverse to the central axis A. Preferably, the third or distal bend 512f is provided on a transverse axis, the transverse axis being represented by axis A2. The first shank first portion 512c' is provided coaxial with the central axis A. The shank second portion 512c" bends relative to the shank first portion 512c' at the first bend 512d, and is in the same axial plane as the shank first portion 512c'. The shank third portion 512c'" bends relative to the shank second portion 512c" at the second bend 512e, and then joins the shank fourth portion 512c"" at the third bend 512f. At the third bend 512f, however, the shank fourth portion 512c"" bends relative to the shank third portion 512c'" in a different axial plane than the shank first portion 512c', shank second portion 512c" and shank third portion 512c'" and the respective first and second bends 512d, 512e. The instrument 510 is shown having a tip 513 that is configured similar to the fan like second tip 223 shown and described in connection with the instrument 210. According to a preferred embodiment, the fan like tip 513 has an inner surface 513a that is concave. The tip 513 may be constructed as described and shown in relation to the tip 223. In the instrument 510 depicted, the concave surface 513a preferably is substantially almost parallel to the handle 511. According to a preferred embodiment, the second end includes a second shank 522, which includes first through fourth shank portions 522c', 522c", 522c'" and 522 c"", respectively, and respective bends 522d, 522e and 522f, similar to the arrangement of bends and shank portions shown in the first end of the instrument 510. A tip 523 is provided at the distal end of the shank 522. The tips 513 and 523, are depicted being constructed similar to the second tip 223 of the instrument 210 shown in FIGS. 2A and 2B, but are oriented as shown in FIG. 5A, 5B. The angular bend of the fourth portion 512c"" orients the tip 513 in a preferred direction for utilization during the subperiosteal augmentation and reconstruction procedures. The tip 523 is configured as a fan shape, where the tip proximal portion 523b joining with the shank shaft 522 at the proximal tip end 523a is configured as a narrower portion, and, from that point distally, the tip 523 widens and fans out over the wider tip distal portion 523c. The tip end 523e preferably has a cutting edge or periphery, similar to the tip 223 of the instrument 210.

According to embodiments, the instrument 510 preferably is constructed with preferred angular dimensions, including a first angle defining a first bend 512d, which is a bend between the first portion 512c' and the second portion 512c", and a second angle defining a second bend 512e which is the bend between the second portion 512c" and the third portion 512c'", and a third angle defining a third bend 512f which is the bend between the third portion 512c'" and the fourth portion 512c"".

According to a preferred embodiment, the instrument 510 preferably is constructed with the fourth portion 512c"" being longer than each of the other three portions (512c', 512c" and 512c'"). The first portion 512c', second portion 512c" and third portion 512c'", may each have similar lengths. For purposes of describing the length of the first portion 512c', the tapered portion 511c of the handle 511 is included in this measurement portion. According to a preferred embodiment, the first, second and third shank portions 512c', 512c", and 512c'", respectively, are each about 10 mm in length. The fourth portion 512c"" inclusive of the tip 513 preferably is about 20 mm. The tip 513 preferably has a length of about 4.5 mm.

Figure 6C:
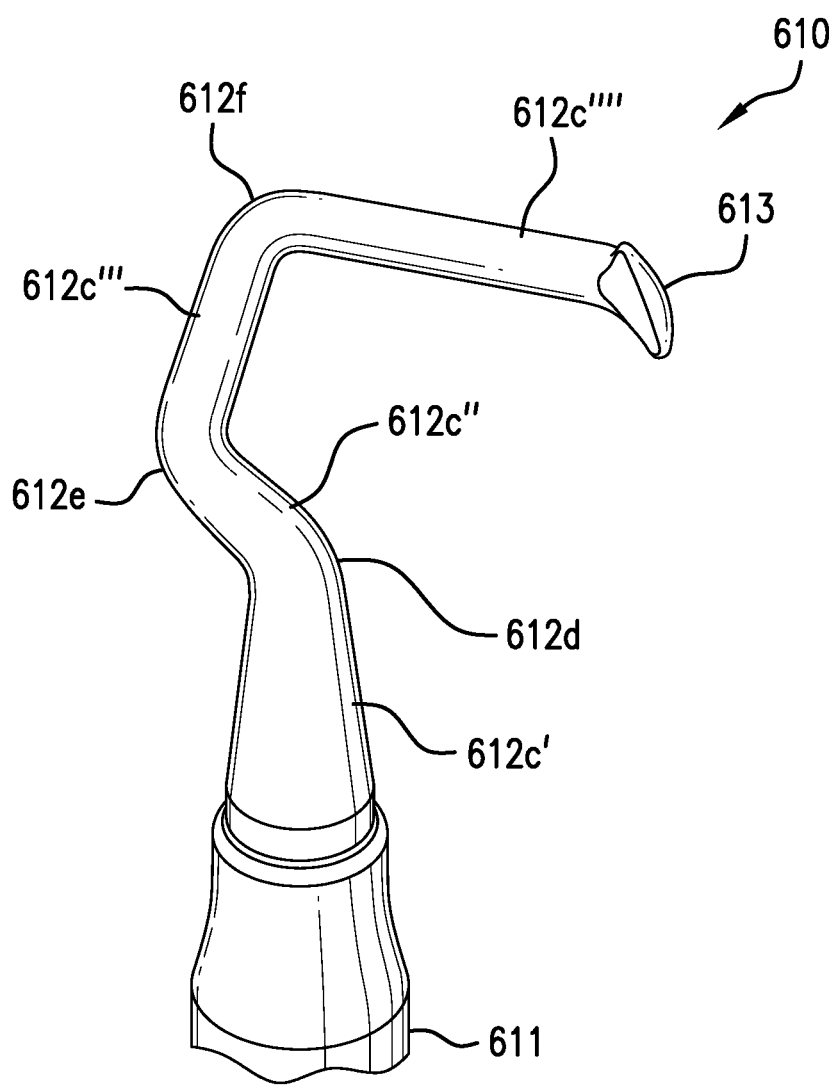
FIG. 6C is an enlarged partial view showing the shank end and tip of the device of FIG. 6A.

Referring to FIGS. 6A and 6B, an alternate embodiment of an elevator instrument 610 is shown. The instrument 610 is similar to the instrument 510, except that the first shank portion 612c' is longer than the second and third shank portions, 612c" and 612c'", respectively, providing an extended reach of the instrument to develop a longer subperiosteal tunnel or to extend the reach within a subperiosteal tunnel. According to a preferred embodiment, the first shank portion 612c' may be about 20 to 40 percent longer than the length of the respective second and third shank portions 612c" and 612c'". According to a preferred embodiment, the length of the second, third and fourth shank portion, respectively, 612c", 612c'", and 612c"", are similar to dimensions discussed in connection with the instrument 510, with the first portion 612c' being provided having a length of about 14 mm. Alternatively, the second portion 612c" may be provided having a greater length, and, according to a preferred embodiment, may be about 12 mm in the example depicted in FIGS. 6A and 6B, where the first portion 612c' is about 14 mm, the third portion 612c'" is about 10 mm and the fourth portion 612c"" including the tip 613 is about 20 mm.

Referring to FIGS. 7A and 7B, an alternate embodiment of an elevator instrument 710 for use in subperiosteal augmentation procedures is shown. The instrument 710 includes a handle 711, a shaft 712 extending from the handle 711, with a tip 713 at the end of the shaft 712. The shaft 712 includes a plurality of shank sections, which in the embodiment depicted are first through fourth shank portions 712c', 712c", 712c'", 712c"", and 712c""', respectively. The shank 712 includes a plurality of bends, which from the proximal shank end to the distal shank end where the tip 713 is located, are depicted as a first bend 712d, a second bend 712e, and a third bend 712f, and a fourth bend 712g. The first bend 712d and second bend 712e are on the same axis, which are in a plane parallel to the central axis A. The third bend 712f is provided transverse to the central axis A. Preferably, the third or distal bend 712f is provided on a transverse axis, the transverse axis being represented by axis A2. The first shank portion 712c' is provided coaxial with the central axis A. The second shank portion 712c" bends relative to the first portion 712c' at the first bend 712d, and is in the same axial plane as the first portion 712c'. The third shank portion 712c'" bends relative to the second shank portion 712c" at the second bend 712e, and then joins the fourth shank portion 712c"" at the third bend 712f. At the third bend 712f, however, the fourth portion 712c"" bends relative to the third portion 712c'" in a different axial plane than the first portion 712c', second portion 712c" and third portion 712c'" and the respective first and second bends 712d, 712e. The fifth shank portion 712c""' bends relative to the fourth shank portion 712c"", at the fourth bend 712g. The fifth shank portion 712c""' bends at the fourth bend 712g relative to the fourth shank section 712c"". The relative bend is along angle Z represented in FIG. 7B, between the fourth shank portion 712c"" and the fifth shank portion 712c""'. As illustrated in the top view of FIG. 7A, the fourth shank portion 712c"" and the fifth shank portion 712c""' may have shaft segments that are coplanar, although other shaft segments may bend making at least some of the respective lengths of the fourth shank portions 712c'''' and the fifth shank portion 712c''''' in different planes. The bend of the third portion 712c''' which is on a transverse axis A2, is shown in FIG. 7B represented by the angular bend where the third portion 712c''' makes an angle Y relative to the second portion 712c'' and the central axis A.

The instrument 710 is shown with a tip 713 at the end of the fifth shank portion 712c'''''. The tip preferably is configured to provide an engaging structure for engaging one or more of the tissue or the bone graft material. According to the exemplary embodiment shown, the tip 713 is configured in a fan like configuration, similar to the tip 513, having an inner surface 713a that is concave. The concave surface 713a preferably is substantially almost parallel to the handle 711. The back of the surface 713b may be convex or flat.

According to a preferred embodiment, the second end includes a second shank 722, which includes first through fifth shank portion 722c', 722c'', 722c''', 722c'''' and 722 c''''', respectively, and respective bends 722d, 722e, 722f and 722g, similar to the arrangement of bends and shank sections shown in the first end of the instrument 710. A tip 723 is provided at the distal end of the shank 722. The tips 713 and 723, are depicted similar to the tip 523 of FIGS. 2A and 2B, but are oriented as shown in FIGS. 7A and 7B. The angular bend of the fifth portion 712c''''' orients the tip 713 is a preferred direction for utilization during the subperiosteal augmentation and reconstruction procedures. The tip 723 is configured as a fan shape, where the tip portion 723a joining with the shank shaft 722 at the proximal tip end is configured as a narrower portion, and, from that point distally, the tip 723 widens and fans out so that the wider portion of the tip 723 is at the tip end 723e.

According to embodiments, the instrument 710 preferably is constructed with preferred angular dimensions, including a first angle defining a first bend, which is a bend between the first portion 712c' and the second portion 712c'', and a second angle defining a second bend which is the bend between the second portion 712c'' and the third portion 712c''', and a third angle defining a third bend which is the bend between the third portion 712c''' and the fourth portion 712c'''', and a fourth angle defining a fourth bend which is the bend between the fourth portion 712c'''' and the fifth portion 712c'''''.

According to a preferred embodiment, the instrument 710 preferably is constructed with the fifth portion 712c''''' being longer than each of the other four portions (712c', 712c'', 712c''' and 712c''''). The first portion 712c', second portion 712c'', third portion 712c''', and fourth portion 712c'''', may each have similar lengths. For purposes of describing the length of the first portion 712c', the tapered portion 711b of the handle 711 is included in this measurement portion. According to a preferred embodiment, the first, second, third and fourth shank portions 712c', 712c'', 712c''' and 712c'''', respectively, are each about 10 mm in length. According to a preferred embodiment, the fourth portion may be slightly longer than the first, second or third portions (such as 12 mm for the fourth portion length and 10 mm for each of the first, second and third portion lengths). The fifth portion 712c''''' inclusive of the tip 713 preferably is about 20 mm. The tip 713 preferably has a length of about 4.5 mm. The fifth portion 712c''''', may extend in a longitudinal direction relative to the fourth portion 712c'''' (as shown by the portion of the fifth portion 712c''''' in FIG. 7A between the fourth portion 712c'''' and the tip 713), so that about 40 percent of the fifth shank portion 712c''''' is radially outward relative to (or beyond) the relatively axial outward reach of the fourth shank portion 712c''''. For example, the fifth shank portion 712c''''' shown in FIG. 7B may be about 20 mm, whereas, the portion of the fifth shank portion 712c''''' shown in FIG. 7A represents about 8 mm of that portion.

Referring to FIGS. 8A and 8B, an alternate embodiment of an instrument 810 is shown. The instrument 810 is similar to the instrument 710, except that the first shank portion 812c' is longer than the second, third and fourth shank portions, 812c'', 812c''', 812c'''', respectively, providing an extended reach of the instrument within a subperiosteal tunnel. The bends shown facilitate positioning and maneuvering the instrument through a subperiosteal tunnel, and to present the tip 813 for engagement with the structure within the tunnel or at the surgical site. According to a preferred embodiment, the first portion 812c' may be about 20 to 40 percent longer than the length of the respective second, third and fourth shank portions 812c'', 812c''' and 812c''''. According to a preferred embodiment, the length of the second, third and fourth and fifth shank portions, respectively, 812c'', 812c''', 812c'''' and 812c''''', may be similar to dimensions discussed in connection with the instrument 710, with the first portion 812c' being provided having a length of about 14 mm, that is, a length longer than the second through fourth portions. Alternatively, one or more of the second, third or fourth portions may be provided having a greater length. For example, the fourth portion 812c'''' may be provided having a greater length, and, according to a preferred embodiment, may be about 12 mm in the example depicted in FIGS. 8A and 8B, where the first portion 812c' is about 14 mm, the second and fourth portions 812c'' and 812c'''', are each about 12 mm, and the third portion 812c''' is about 10 mm. The fifth portion 812c''''' including the tip 813 is about 20 mm.

Figure 9A:
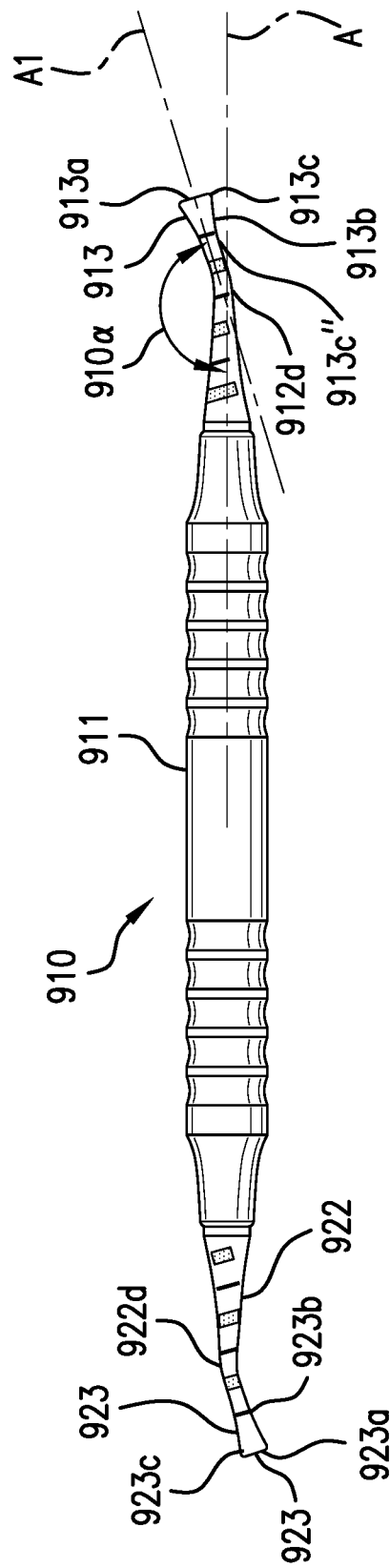
FIG. 9A is a top plan view of a ninth alternate embodiment of device according to the invention configured as a condenser.
Figure 9B:
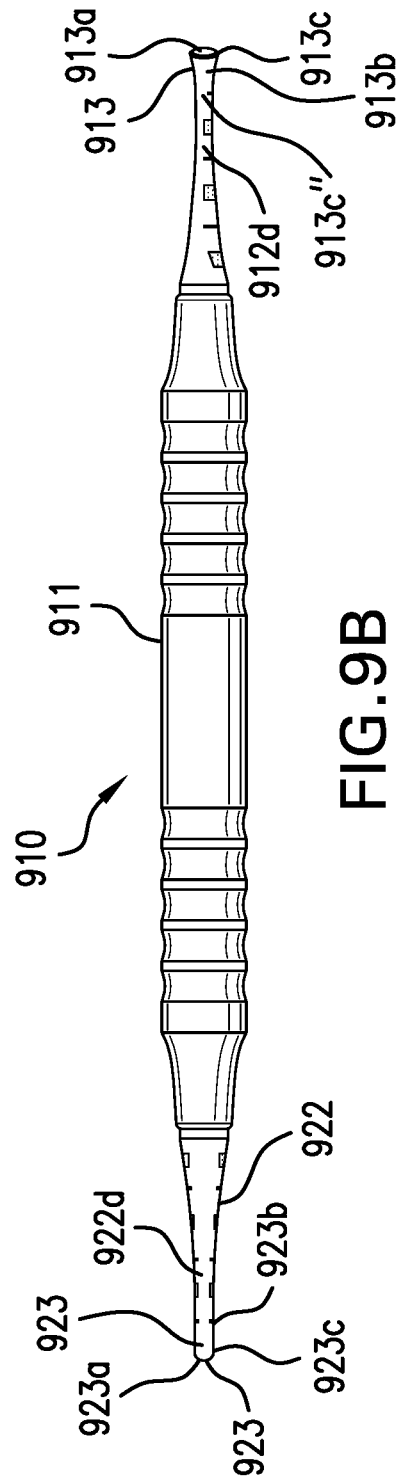
FIG. 9B is a right side elevation view of the device of FIG. 9A.
Figure 9C:
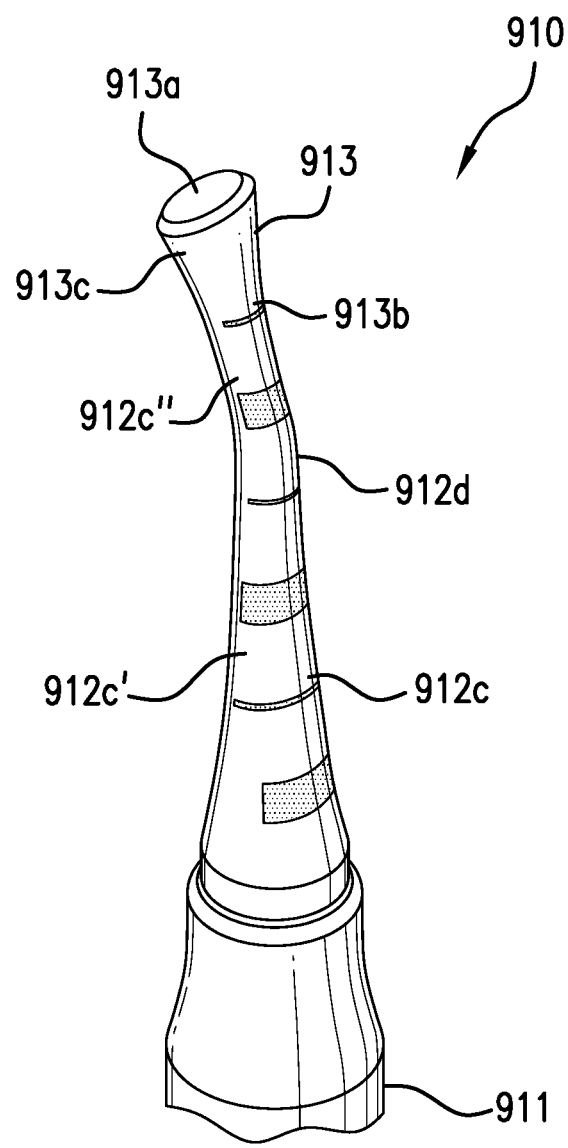
FIG. 9C is an enlarged partial view showing the shank end and tip of the device of FIG. 9A

Referring to FIGS. 9A, 9B and 9C, an instrument for conducting subperiosteal augmentation and reconstruction procedures is depicted, configured as a condenser instrument 910 is shown having a handle 911 with a body 911a, a first tapered portion 911b at one end of the body 911a, and a second tapered portion 911c at the other end of the body 911a. The condenser has a shank 912, with a first shank shaft portion 912c' and a second shank shaft portion 912c''. The second shank shaft portion 912c'' bends relative to the first shank shaft portion 912c' at an angle relative to the central axis A of the instrument 910. According to a preferred embodiment, the bend is along the central axis A and the central axis A2 of the second shaft portion 912c'', with angle alpha 910 (α910) representing the angle of the bend. The instrument 910 depicted preferably includes a rounded tip 913, which, according to a preferred embodiment, is oval shaped, with an oval face 913a. The tip 913 preferably extends from a narrower portion 913b from the location where the tip 913 joins the distal end of the second shank shaft portion 912c''. The tip 913 widens from the narrower proximal portion 913b distally to the tip end 913c. Preferably, the instrument tip 913 may have an oval shape, which may comprise an oval body with a thickness. The thickness preferably may be cross-sectionally oval, or, according to some embodiments, may be a flattened oval shape, with the oval shape being more pronounced closest to the distal tip end 913c supporting the tip surface 913a. Alternate views in FIGS. 9B-9C depict the condenser instrument 910 and tip 913.

According to a preferred embodiment, an oval tip, such as, for example, the oval tip 913, may be constructed to have a ratio of a long diameter width to the short diameter (height) of about 9 to 5, and more preferably from about 9 to 7 in the exemplary embodiment depicted. According to a preferred configuration, a condenser instrument 910 may be configured with an oval tip 913 which, preferably at the tip surface 913a, has a long width diameter of 4.5 mm and a shorter or height diameter of about 3.5 mm. The thickness of the long width preferably narrows from the tip surface 913a toward the tip proximal end 913b. The thickness of the short or height diameter also may narrow from the tip surface 913a at the distal tip end 913c to the proximal end 913b.

The instrument 910 preferably has a second shank 922 on the opposite handle end, shown comprising a first shank portion 922c' and second shank portion 922c" with a second tip 923 joining the distal end of the second shank portion 922c". In the embodiment illustrated in FIGS. 9A to 9C, the second tip 923 is provided as a smaller tip relative to the first tip 913. For example, according to a preferred embodiment, the second tip may be provided having a ratio of a long diameter width to the short diameter (height) of about 9 to 5, and more preferably, in the exemplary embodiment depicted, from about 7 to 5. According to a preferred configuration, the second tip 923 may be constructed having a long width diameter of 3.5 mm and a shorter or height diameter of about 2.5 mm. The thickness of the long width preferably narrows from the tip surface 923a toward the tip proximal end 923b. The thickness of the short or height diameter also may narrow from the tip surface 923a at the distal tip end 923c to the proximal end 913b. A beveled or angled edge may be provided at the tip end 923e near the tip surface 923a. A similar beveled end (not shown) may also be provided on the first tip 913. The shank 922 preferably also has a bend 912d therein similar to the shank 912 of the first end.

Figure 10A:
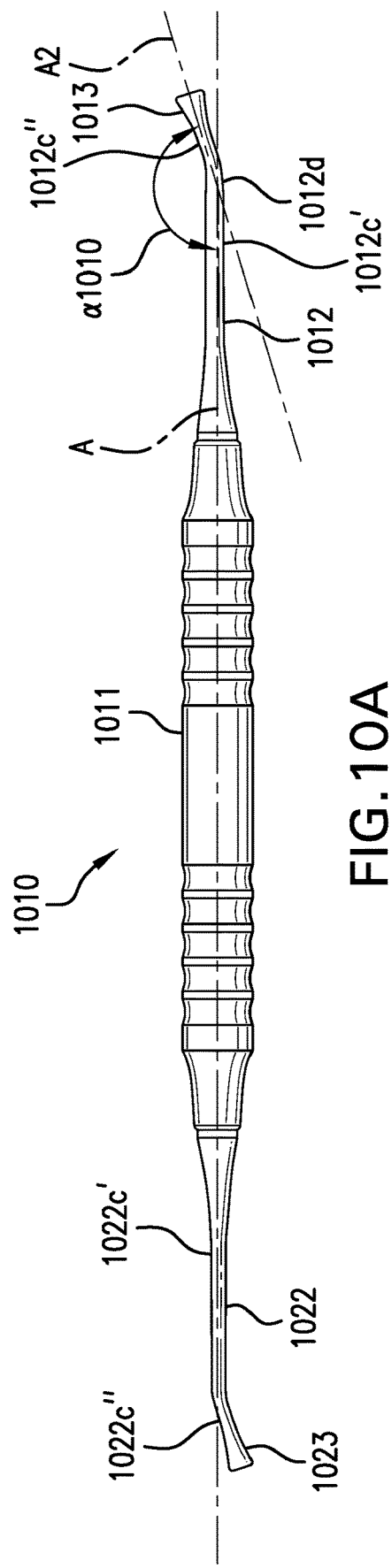
FIG. 10A is a top plan view of a tenth alternate embodiment of device according to the invention configured as a condenser, being similar to the device of FIG. 9A, having a longer reach.
Figure 10B:
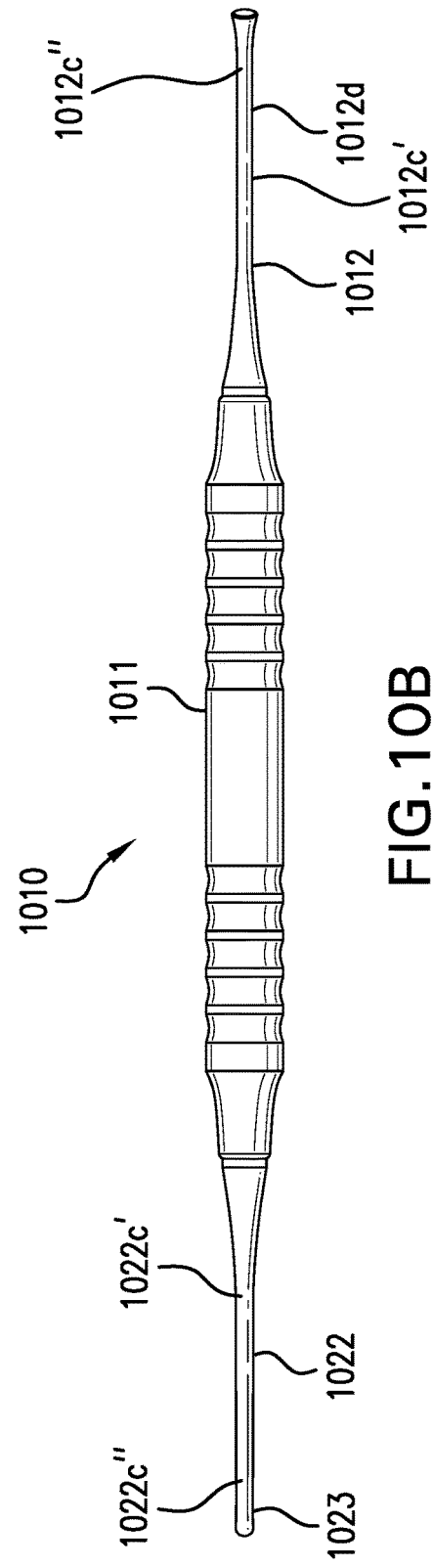
FIG. 10B is a right side elevation view of the device of FIG. 10A.

Referring to FIG. 10A, an alternate embodiment of an instrument 1010 configured as a condenser is shown. The condenser instrument 1010 is similar to the instrument 910 shown in FIG. 9A, but having an elongated shank shaft 1012, with a bend 1012d. The shank shaft first portion 1012c' preferably may be provided similar to the shank shaft portion 912c' of the instrument 910, but in the embodiment illustrated in FIG. 10A, the instrument 1010 has a longer reach due to a longer shank shaft second portion 1012c". The tip 1013 may be the same as the tip 913 shown and described herein, which according to a preferred embodiment is configured as an oval shape. The instrument 1010 also has a handle 1011, with a handle body 1011a, a tapered first portion 1011b, and tapered second portion 1011c. According to the embodiment illustrated, the instrument 1010 is configured as a condenser, and the angle alpha 1010 ($\alpha 1010$), is greater than the corresponding angle ($\alpha 910$) of the instrument 910, to provide an extended reach. Preferably, the extension of the tip 1013 may be axially away from the central axis A, an equal distance as the axial distance of the tip 913 in the instrument 910 of FIG. 9A, away from the central axis A of the instrument 910. The instrument 1010 also includes a second end, having a second shank 1022 on the opposite side of the handle 1011. The second shank 1022 includes a shank shaft first portion 1022c', providing a longer reach similar to the shank shaft first portion 1012c', and includes a second shank shaft portion 1012c" with a second tip 1023. The second tip 1023 preferably is configured similar to the second tip 923 provided in connection with the instrument 910.

Features discussed and shown herein in conjunction with one or more embodiments of the devices may be combined with one or more features and implemented together. In addition, although instruments are depicted with shanks that may be of similar length at each handle end, shanks of different lengths may be provided, according to some alternate embodiments. In addition, as discussed above in connection with the shank 112, the outer surface of the instruments shown and described herein, including on the shanks, may include a scale thereon that provides a depth indicator. Shanks preferably may have a series of evenly spaced markings which may be visibly provided thereon to mark the depth at a point along the shank, from the tip end. The marking depth indication provides a depth indication to the user when the instrument is inserted in a subperiosteal tunnel or otherwise penetrates tissue, so the user will know the penetration depth of the instrument (when the instrument portion, such as the shank, is within the tunnel and not visible to the user). While the devices of the invention have been disclosed in detail, and the preferred embodiments and best mode for practice of the invention have been similarly disclosed, the scope of exclusive rights to which the invention is entitled is defined by the claims appended hereto and by equivalents that perform substantially the same function in substantially the same way to achieve the same result.

Figure 11A:
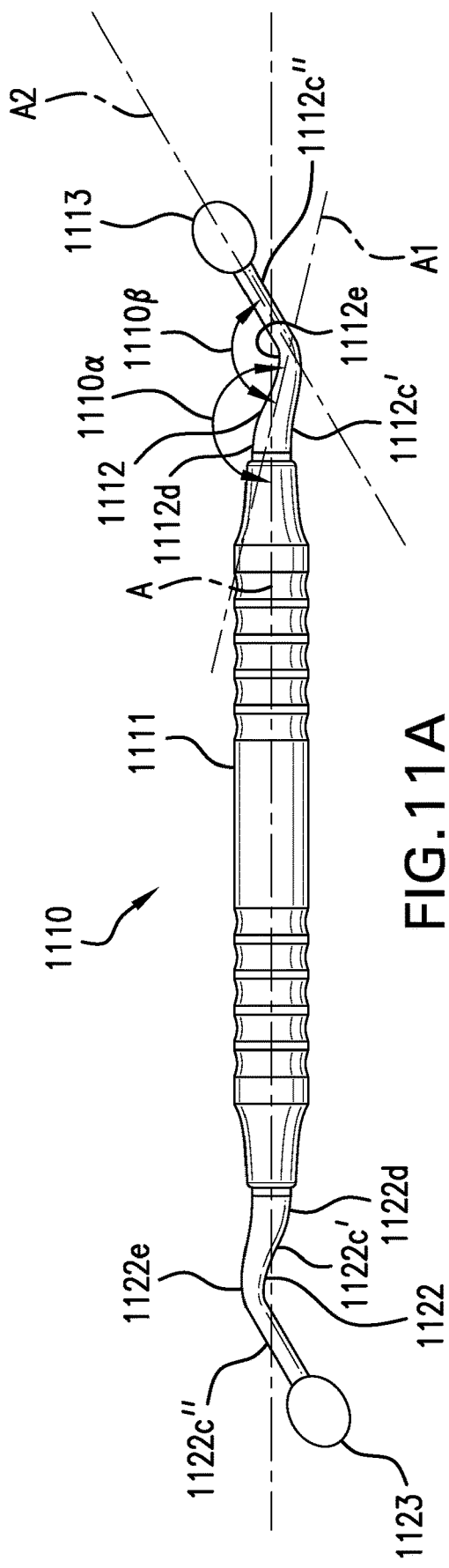
FIG. 11A is a top plan view of an eleventh alternate embodiment of device according to the invention configured as a compactor.
Figure 11B:
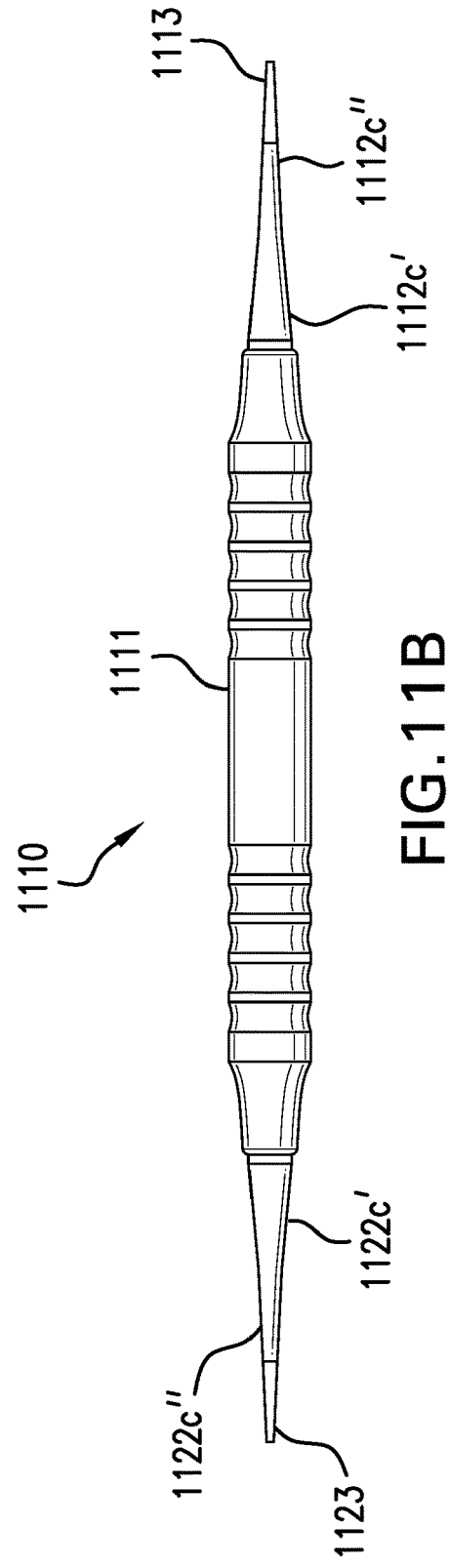
FIG. 11B is a right side elevation view of the device of FIG. 11A.
Figure 11C:
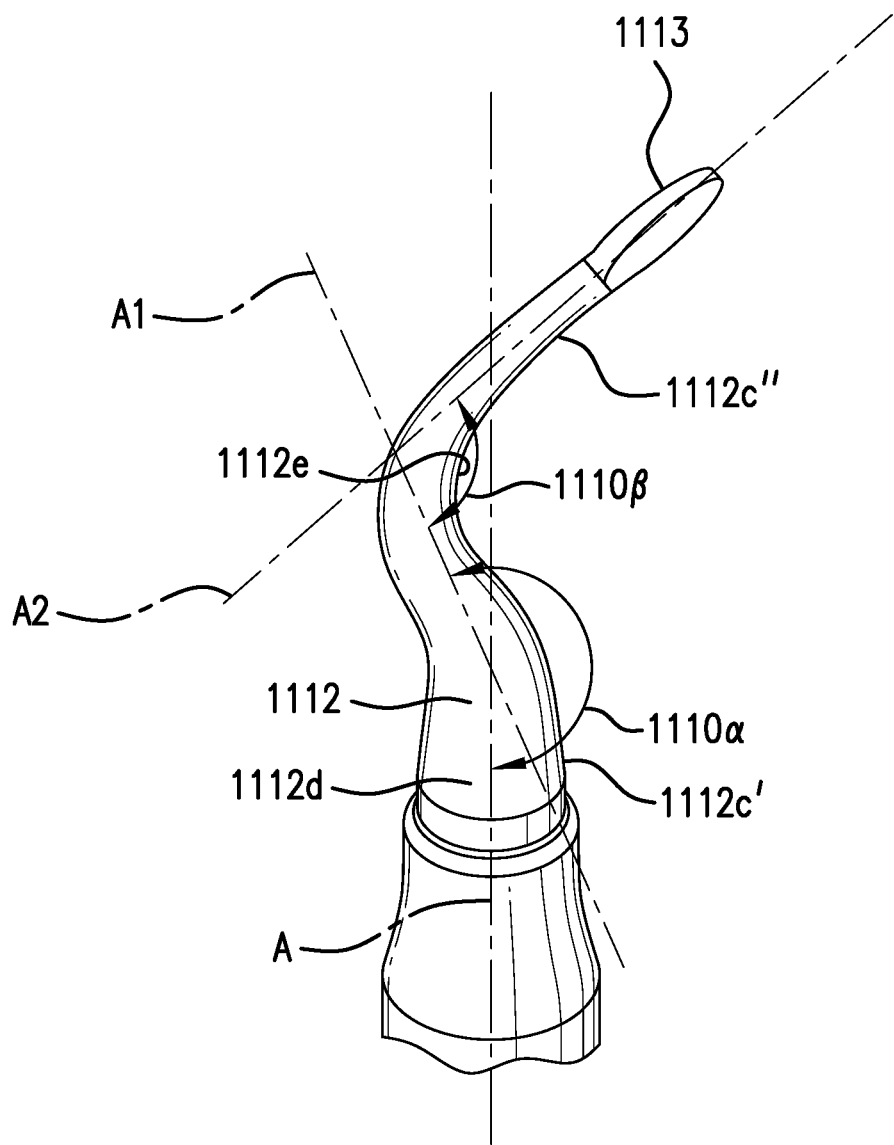
FIG. 11C is an enlarged partial view showing the shank end and tip of the device of FIG. 11A.

Referring to FIGS. 11A to 11C, a compactor 1110 is shown having a handle 1111 with a first shank 1112 at the first handle end, and a tip 1113 at the distal end of the shank 1112. The shank 1112 is shown comprising a first shank portion 1112c' and a second shank portion 1112c", with a first bend 1112d at the first shank portion 1112c' joining the handle 1111, and a second bend 1112e where the first shank portion 1112c' and second shank portion 1112c" join. The tip 1113 is shown at the distal end of the second shank portion 1112c". The instrument 1110 is configured as a compactor, which may be utilized in a subperiosteal tunnel and/or surgical site to compact tissue or bone material, including bone graft material. The instrument 1110 preferably is configured to be maneuverable within the mucosa and/or subperiosteal tissue to apply a force in a desired direction that may be directed by movements of the handle 1111. For example, the handle 1111 may be manipulated by moving it forward or rearward angling it, and/or rotating it, or by combinations of these movements consecutively, or simultaneously, to direct the tip 1113. As shown in FIGS. 11A, 11B, 11C, the tip 1113 is oval in configuration with a substantially flat profile, having a thickness substantially less than the length and width of the oval. The tip 1113 and shank 1112 (or portion thereof) may be introduced in a subperiosteal tunnel and may be maneuvered to compact the graft. For example, where graft material is introduced at a remote surgical site, the instrument shank 1112 may be directed through a tunnel and to the surgical site, where the tip 1113 can be manipulated, preferably via the handle 1111, to engage the graft material at the surgical site. Preferably, the tip 1113 is linear and is aligned with the axis of the second shank portion 1112c" to which the tip 1113 is joined.

According to preferred embodiments, the instrument 1110 may be provided with markings on the shank. Preferably, the markings are provided on a linear scale to mark the linear distance from the tip to a location on the shank 1112. For example, according to a preferred embodiment, the markings may be designated in units, such as millimeters, and may be marked periodically, such as every 1 mm, 3 mm, 5 mm, or other arrangement. The marking indicia may be etched, engraved, or applied by other suitable marking methods, suitable for being able to insert the marked shank 1112 into tissue, including a subperiosteal tunnel and surgical site. The linear markings, for example, measure a length along the instrument central axis, from the tip end 1113e. As shown in FIG. 11B, the markings are linear, and therefore, any measurements are continued to be measured linear, along the central axis, and in the embodiment illustrated, are not necessarily measured from the axis of the shank 1112 (which has a greater length than the portion of the instrument central axis that the shank 1112 spans).

According to a preferred embodiment, the oval tip 1113 may be provided having a length that is axially longer than the width, as illustrated in FIGS. 11A-11C. One preferred ratio of the length to width is about 11 to 8. For example, according to a preferred instrument embodiment, the oval may have a length of 5.5 mm and a width of about 4 mm. The instrument 1110 is shown having a thickness that is less than the width of the oval. Some preferred embodiments provide a thickness that is about 1 to 3 mm in thickness, and more preferably from about 1.5 to 2.5 mm.

The compactor instrument 1110 preferably is configured with a second shank portion 1112c" that is longer than the first shank portion 1112c'. The first shank portion 1112c' preferably, at the first bend 1112d is angularly bent relative to the handle 1111, as measured in reference to the instrument central axis A and the central axis A1 of the first shank portion 1112c' at an angle alpha (1110α). The first angle 1110α preferably is provided to be less than about 45 degrees, and more preferably, between about 15 and 35 degrees.

The second shank portion 1112c" preferably, at the second bend 1112e is angularly bent relative to the first shank portion 1112c', at an angle beta (1110β), as measured between the central axis A2 of the second shank portion 1112c" and the central axis A1 of the first shank portion 1112c'. The second angle 1110β preferably is provided to be greater than the first angle alpha (1110α). The second angle 1110β preferably is less than 180 degrees, and more preferably is between about 120 to 170 degrees. According to preferred embodiments, the compactor 1110 preferably may have a second end with a second shank 1122 extending from the handle 1111. According to some embodiments, the second shank 1122 may be constructed similar to the first shank 1112, with a second tip 1123 provided on the second shank portion 1122c", and with the second shank portion 1122c" being provided at a bend 1122d where the second shank portion 1122c" joins the first shank portion 1122c'. The first shank portion 1122c' is shown extending from the handle 1111. The second tip 1123 may be configured to be the same as the first tip 1113. According to some alternate embodiments, the second tip 1123 may be different than the first tip 1113. For example, the second tip may be provided having a different size, where the tip is relatively smaller or larger. The second tip may maintain proportions of the first tip oval configurations (and/or thicknesses) although it may be smaller or larger in some alternate embodiments. According to some other embodiments, the second tip may be provided with different proportions, and/or thicknesses.

According to a preferred embodiment, the compactor 1110 is constructed with the portion of the shank shaft 1112c between the first bend 1112d and second bend 1112e being about 14 mm, and with the portion between the second bend 1112e to the tip 1113, inclusive of the tip length, being about 22 mm. Similarly, the second shank 1122c may be constructed with similar dimensions.

Referring to FIGS. 12A and 12B, an alternate embodiment of an instrument 1210 configured as a compactor is shown. The compactor instrument 1210 is similar to the compactor instrument 1110 of FIGS. 11A, 11B and 11C, except that each shank 1212, 1223 is longer, and the angles of the shank bends, the first angle alpha (1210α) and second angle beta (1210β) in the instrument 1210 are provided to produce less of a bend. The first angle alpha (1210α) of the instrument 1210 is less than the corresponding angle (1110α) of the instrument 1110. The second angle beta (1210β) of the instrument 1210 is greater than the second angle beta (1110β) of the instrument 1110. The first shank shaft portion 1212c' on the first end of the instrument 1210 is longer in relation to the first shank shaft portion 1112c' in the instrument 1110 depicted in FIGS. 12A and 12B, as is the second shank portion 1212c" which is longer than the corresponding second shank portion 1112c" of the instrument 1110. In the longer instrument 1210, the tip 1213 is distally further from the handle 1211. The shank 1212 is constructed to have less pronounced angular bends at the first bend 1212d and second bend 1212e so as to provide a maximum instrument width that includes deviations from the central axis A, on either side. According to some embodiments, the axial width or window for the instrument 1110 may be the same window as for the instrument 1210, with the additional shank length being accommodated by a reduction in the outward deviation of the shaft relative to the central axis A. The second instrument end includes a second tip 1223 provided at the end of the second shaft 1222. The second shaft 1222 extends from the handle 1211, and preferably from the tapered portion 1211c and to where it joins the tip 1223 at the distal shank end. Similar to the first shaft portion 1212c' and second shaft portion 1212c" of the first shaft 1212, the second shaft 1222 includes a first shaft portion 1222c' and second shaft portion 1222c".

According to a preferred embodiment, the compactor 1210 is constructed with the portion of the shank shaft 1212c between the first bend 1212d and second bend 1212e being about 19 mm, and with the portion between the second bend 1212e to the tip 1213, inclusive of the tip length, being about 27 mm. Similarly, the second shank 1222c may be constructed with similar dimensions. In a preferred embodiment, each oval tip 1213, 1223, preferably, is similar to the oval tip 1113 and 1123 of the instrument 1110. According to a preferred embodiment, the tips 1213 and 1223, may be about 5.5 mm in length, with a width of about 4 mm.

According to preferred embodiments, the instrument tips, such as, for example, the tips 1113, 1123, 1213, and 1223, preferably are oval in configuration and may have a tapered thickness, which may be wedge shaped, as illustrated in the side views of FIGS. 11A and 12A, for the respective instruments 1110 and 1210. The tapered tip 1113, for example, may be provided with both sides being tapered to converge. For example, according to the embodiment illustrated in FIG. 11B, the tip surfaces are shown converging toward the axis A from the proximal tip end to the distal tip end. Similarly, the tip 1213 of the instrument 1210 shown in FIG. 12B is shown with the converging surfaces. The tips of the other ends of the instruments (1123 and 1223) also may be similarly configured. According to some alternate embodiments, a single side of the tip 1113 may converge and the other side may remain axially straight. Preferably, the tip 1113 includes an end portion with a surface 1113e for engaging with material, such as, for example, bone graft material, to position or compact the material into place.

Features discussed and shown herein in conjunction with one or more embodiments of the devices may be combined with one or more features and implemented together. In addition, although instruments are depicted with shanks that may be of similar length at each handle end, shanks of different lengths may be provided, according to some alternate embodiments. In addition, as discussed above in connection with the shank 112, the outer surface of the instruments shown and described herein, including on the shanks, may include a scale thereon that provides a depth indicator.

Shanks preferably may have a series of evenly spaced markings which may be visibly provided thereon to mark the depth at a point along the shank, from the tip end. The marking depth indication provides a depth indication to the user when the instrument is inserted in a subperiosteal tunnel or otherwise penetrates tissue, so the user will know the penetration depth of the instrument (when the instrument portion, such as the shank, is within the tunnel and not visible to the user). While the devices of the invention have been disclosed in detail, and the preferred embodiments and best mode for practice of the invention have been similarly disclosed, the scope of exclusive rights to which the invention is entitled is defined by the claims appended hereto and by equivalents that perform substantially the same function in substantially the same way to achieve the same result.

What is claimed is:

1. A surgical instrument for subperiosteal tunneling and bone grafting procedures, comprising:
   a) a handle;
   b) a shank extending from the handle;
   c) a tip provided on the shank;
   d) wherein, upon moving said handle, said shank is configured to manipulate the tip in one or more directions; and
   e) wherein said tip has a distal portion and a proximal portion, wherein said distal portion comprises a convex curved portion having a leading edge thereon, said curved portion leading edge terminating on each side at a respective terminal edge that is located at each side of the widest width of the tip, and wherein said proximal portion comprises a tapering portion, said tapering portion tapering from each respective terminal edge of said tip to said shank.

2. The instrument of claim 1, wherein said handle rotation imparts a force from said tip in a direction different than the handle movement.

3. The instrument of claim 1, wherein said tip comprises a fan-like configuration having an arcuate periphery with a sharp edge provided on said arcuate periphery.

4. The instrument of claim 3, wherein the distal portion forms the end of the instrument, and wherein the proximal portion joins with the shank, wherein said proximal portion and said distal portion join to form a width of the tip, wherein said distal portion includes said sharp edge.

5. The instrument of claim 4, wherein said proximal portion tapering portion includes a first side edge and a second side edge, wherein each of said first side edge and said second side edge joins with said shank at one end thereof and joins with said distal portion at the other end thereof.

6. The instrument of claim 5, wherein each of said first side edge and said second side edge are inwardly curved relative to an axial centerline.

7. The instrument of claim 6, wherein said first side edge joins with said distal tip portion to form a first corner.

8. The instrument of claim 7, wherein said second side edge joins with said distal tip portion to form a second corner.

9. The instrument of claim 8, wherein said first corner and said second corner comprise sharp edges.

10. The instrument of claim 3, wherein said tip has an upper surface and a lower surface, and wherein said upper surface is concave.

11. The instrument of claim 9, wherein said tip has an upper surface and a lower surface, and wherein said upper surface is concave.

12. The instrument of claim 11, wherein said shank has a central axis, and wherein said tip has a central axis, and wherein said tip is angled relative to said shank such that the angle between said tip central axis and said shank central axis, as determined from the concave surface of said tip, is less than 180 degrees.

13. The instrument of claim 10, wherein said shank has a central axis, and wherein said tip has a central axis, and wherein said tip is angled relative to said shank such that the angle between said tip central axis and said shank central axis, as determined from the concave surface of said tip, is less than 180 degrees, and
   wherein said handle has a first end and a second end, with a first shank at said first handle end and a second shank at said second handle end, and wherein said tip comprising a fan-like configuration comprises a first tip provided at the end of said first shank, and wherein a second tip is provided at the end of said second shank.

14. The instrument of claim 13, wherein said second tip comprises a triangular shaped tip.

15. The instrument of claim 13, wherein said second tip has a fan-like configuration.

16. The instrument of claim 13, wherein said first shank and said first tip comprise a unitary continuous structure extending from the first handle end, and wherein said second shank and said second tip comprise a unitary continuous structure extending from the second handle end.

17. The instrument of claim 10, wherein said tip lower surface is convex.

18. The instrument of claim 11, wherein said tip lower surface is convex.

19. The instrument of claim 1, wherein said tip has an end, and wherein said shank has markings provided thereon that indicate the depth of said marking to the tip end.

20. The instrument of claim 1, wherein said shank includes at least one bend therein.

21. The instrument of claim 20, wherein said shank includes a first shank portion extending from said handle, a second shank portion joining with said first shank portion at said at least one bend, and wherein said tip is provided on said shank.

22. The instrument of claim 21, wherein the instrument has a longitudinal central instrument axis A, wherein said shank has a first bend and a second bend, wherein said shank includes a shank first portion that meets the shank second portion at the second bend, wherein the shank at the first bend is angled away from the instrument central axis A, at an angle represented by a first angle alpha ($\alpha$), wherein the shank second portion bends inwardly toward the instrument central axis A relative to the first shank portion at a second angle represented by angle beta ($\beta$) where angle beta ($\beta$) is the angle between the first shank portion and the second shank portion, and wherein the first angle alpha ($\alpha$), that the shank first portion makes with the instrument central axis A is relatively smaller than the second angle beta ($\beta$) that the shank first portion makes with the shank second portion.

23. The instrument of claim 22, wherein the first angle alpha ($\alpha$) is about 30 degrees, and whereas the second angle beta ($\beta$) is about 120 degrees.

24. The instrument of claim 23, wherein the shank includes a shank first portion, a shank second portion, a shank third portion and a shank fourth portion, a first bend, a second bend, and a third bend, wherein said first bend and said second bend are on the same axis which is in a plane parallel to the instrument central axis A, and wherein the third bend is provided transverse to the instrument central axis A.

25. The instrument of claim 23, wherein said third bend is provided on a transverse axis that is transverse to said instrument central axis A.

26. The instrument of claim 24, wherein the first shank portion is coaxial with the instrument central axis A, wherein the second shaft portion bends relative to the first shank portion at the first bend and is in the same axial plane as the first shank portion, wherein the third shank portion bends relative to the second shank portion at the second bend, wherein the third shank portion joins the fourth shank portion at the third bend, wherein at the third bend the fourth shank portion bends relative to the third shank portion in a different axial plane than that of the first shank portion, second shank portion and third shank portion, and the respective first and second bends.

27. The instrument of claim 1, wherein the tip has a fan-like configuration with an inner surface that is concave.

28. The instrument of claim 27, wherein the plane of the concave surface is situated in a direction that is substantially parallel to the handle.

29. The instrument of claim 1, wherein the handle has a first end and a second end, and including a first shank at said first handle end, and a second shank at said second handle end, and wherein a first tip is provided at the end of said first shank and wherein a second tip is provided at the end of said second shank.

30. The instrument of claim 1, wherein said distal portion edge comprises a radial edge defined by a radius, and wherein the radius has a center point that is located within the area of the tip.

31. The instrument of claim 20, wherein said instrument has an axial centerline, wherein said shank portion has at least one bend that crosses said axial centerline in at least one location along said axial centerline, and wherein said tip edge is located at said axial centerline or crosses over said axial centerline.

* * * * *